US011576960B2

(12) United States Patent
Kang et al.

(10) Patent No.: US 11,576,960 B2
(45) Date of Patent: Feb. 14, 2023

(54) RESPIRATORY SYNCYTIAL VIRUS (RSV) VACCINES

(71) Applicant: Georgia State University Research Foundation, Inc., Atlanta, GA (US)

(72) Inventors: Sang-Moo Kang, Lilburn, GA (US); Youri Lee, Norcross, GA (US); Eunju Ko, Rockville, MD (US); Young-Man Kwon, Johns Creek, GA (US); Ki-Hye Kim, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 17/043,979

(22) PCT Filed: Mar. 29, 2019

(86) PCT No.: PCT/US2019/024895
§ 371 (c)(1),
(2) Date: Sep. 30, 2020

(87) PCT Pub. No.: WO2019/191623
PCT Pub. Date: Oct. 3, 2019

(65) Prior Publication Data
US 2021/0052718 A1 Feb. 25, 2021

Related U.S. Application Data

(60) Provisional application No. 62/650,400, filed on Mar. 30, 2018.

(51) Int. Cl.
*A61K 39/12* (2006.01)
*A61K 39/00* (2006.01)

(52) U.S. Cl.
CPC ...... *A61K 39/12* (2013.01); *A61K 2039/5252* (2013.01); *A61K 2039/5258* (2013.01); *A61K 2039/55594* (2013.01)

(58) Field of Classification Search
None
See application file for complete search history.

(56) References Cited

U.S. PATENT DOCUMENTS 7,169,395 B1 * 1/2007 Cates .............. A61K 39/12
424/202.1
2004/0028698 A1 2/2004 Colau et al.
(Continued)

FOREIGN PATENT DOCUMENTS

WO 02/28426 A1 4/2002
WO 2017/070622 A1 4/2017

OTHER PUBLICATIONS

McLellan et al. Science. 2013; 342 (6158): 592-598).*
(Continued)

*Primary Examiner* — Shanon A. Foley
(74) *Attorney, Agent, or Firm* — Thomas | Horstemeyer, LLP

(57) ABSTRACT

Disclosed are vaccines capable of achieving protection against RSV while avoiding vaccine-enhanced disease (VED). In particular, vaccine constructs have been molecularly designed and genetically engineered to comprise RSV fusion (F) protein displayed on the surface of a particle, such as a virus-like particles (VLP) and low temperature-prepared split RSV. In some embodiments, the RSV F protein is in a pre-fusion F conformation. Also disclosed a variants and combinations of split RSV and RSV F DNA vaccine with pre-fusion F and enhanced efficacy. In addition, disclosed split RSV vaccines containing pre-fusion F conformation and combination adjuvants MPL and CpG.

14 Claims, 22 Drawing Sheets
Specification includes a Sequence Listing.

(56) References Cited

U.S. PATENT DOCUMENTS

| | | |
|---|---|---|
| 2008/0233150 A1 | 9/2008 | Smith |
| 2009/0081728 A1 | 3/2009 | Murphy et al. |
| 2010/0239617 A1* | 9/2010 | Pushko .................. C12N 7/00 435/235.1 |
| 2011/0097358 A1* | 4/2011 | Galarza .................. A61P 31/16 424/202.1 |
| 2011/0305727 A1* | 12/2011 | Swanson ............ C07K 16/1027 424/211.1 |
| 2017/0298101 A1 | 10/2017 | Kwong et al. |
| 2020/0030436 A1* | 1/2020 | Pushko ................ A61K 9/0019 |
| 2021/0052718 A1* | 2/2021 | Kang .................. C07K 14/005 |

OTHER PUBLICATIONS

Cullen et al. (Vaccines. 2019; 7 (21): doi:10.3390).*
Seq ID No. 2 alignment with UniProt db access No. C3UPB8_9MONO Jun. 2009 by Moore et al.*
Seq ID No. 3 alignment with UniProt db access No. C3UPB8_9MONO Jun. 2009 by Moore et al.*
Moore et al. (Journal of Virology. May 2009; 83 (9): 4185-4194).*
Stobart et al. (Nature Communications. Apr. 2016; 7: 13916).*
Zimmer et al. (Journal of Biological Chemistry. 2001; 276 (34): 31642-31650).*
Seq ID No. 3 alignment with Issued_Patents_AA database 15633578 corresponding to USPgPub 20170298101 Oct. 2017.*
Rigter et al. (PLoSOne. 2013; 8 (8): e71072).*
Ruiz-Arguello et al. (Journal of General Virology. 2004; 85: 3677-3687).*
International Search Report issued for PCT/US2019/024895 dated Jul. 11, 2019.
Cullen, Lori McGinnes, et al., "Cotton rat immune responses to virus-like particles containing the pre-fusion form of respiratory syncytial virus fusion protein," Journal of Translational Medicine, vol. 66, No. 7 (2015), pp. 7444.
McLellan J. S., et al., "Structure-Based Design of a Fusion Glycoprotein Vaccine for Respiratory Syncytial Virus," Scient, vol. 342, No. 6158 (2013), pp. 592-598.
Smith, Gale, et al., "Respiratory Syncytial Virus Fusion Glycoprotein Expressed in Insect Cells Form Protein Nanoparticles That Induce Protective Immunity in Cotton Rats," Plos One, vol. 7, No. 11 (2012), (12 pages).
Rigter, Alan, et al., "A Protective and Safe Intranasal RSV Vaccine Based ona Recombinant Prefusion-Like Form of the F Protein Bound to Bacterium-Like Particles," Plos One, vol. 8, No. 8 (2013), (14 pages).
Moore, M. L., et al., "A Chimeric A2 Strain of Respiratory Syncytial Virus (RSV) with the Fusion Protein of RSV Strain Line 19 Exhibits Enhanced Viral Load, Mucus, and Airway Dysfunction," Journal of Virology, vol. 83, No. 9 (2009), pp. 4185-4194.
Youri, Lee, et al., "The efficacy of inactivated split respiratory syncytial virus as a vaccine candidate and the effects of novel combination adjuvants," Antiviral Research, vol. 168 (2019), pp. 100-108.
Young-Man, Kwon, et al., "Antigenicity and immunogenicity of unique prefusion-mimic F proteins presented on enveloped virus-like particles," Vaccine, vol. 37, No. 44 (2019), pp. 6656-6664.
Extended Search Report, EP Patent Application No. 19777069.6, dated Jun. 3, 2022 (16 pages).

* cited by examiner

```
                         SEQUENCE LISTING

<160> NUMBER OF SEQ ID NOS: 8

<210> SEQ ID NO 1
<211> LENGTH: 566
<212> TYPE: PRT
<213> ORGANISM: Artificial Sequence
<220> FEATURE:
<223> OTHER INFORMATION: Synthetic Construct

<400> SEQUENCE: 1

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Lys Ala Lys Lys Glu Leu Pro
            100                 105                 110

Arg Phe Met Asn Tyr Thr Leu Asn Asn Ala Lys Lys Thr Asn Val Thr
        115                 120                 125
```

-continued

```
Leu Ser Lys Lys Gln Lys Gln Gln Thr Ser Ala Ile Ala Ser Gly Val
130             135                 140

Ala Val Cys Lys Val Leu His Leu Glu Gly Glu Val Asn Lys Ile Lys
145                 150                 155                 160

Ser Ala Leu Leu Ser Thr Asn Lys Ala Val Val Ser Leu Ser Asn Gly
                165                 170                 175

Val Ser Val Leu Thr Phe Lys Val Leu Asp Leu Lys Asn Tyr Ile Asp
            180                 185                 190

Lys Gln Leu Leu Pro Ile Leu Asn Lys Gln Ser Cys Ser Ile Ser Asn
                195                 200                 205

Ile Glu Thr Val Ile Glu Phe Gln Gln Lys Asn Asn Arg Leu Leu Glu
210                 215                 220

Ile Thr Arg Glu Phe Ser Val Asn Ala Gly Val Thr Thr Pro Val Ser
225                 230                 235                 240

Thr Tyr Met Leu Thr Asn Ser Glu Leu Leu Ser Leu Ile Asn Asp Met
                245                 250                 255

Pro Ile Thr Asn Asp Gln Lys Lys Leu Met Ser Asn Asn Val Gln Ile
                260                 265                 270

Val Arg Gln Gln Ser Tyr Ser Ile Met Cys Ile Ile Lys Glu Glu Val
            275                 280                 285

Leu Ala Tyr Val Val Gln Leu Pro Leu Tyr Gly Val Ile Asp Thr Pro
290                 295                 300

Cys Trp Lys Leu His Thr Ser Pro Leu Cys Thr Thr Asn Thr Lys Glu
305                 310                 315                 320

Gly Ser Asn Ile Cys Leu Thr Arg Thr Asp Arg Gly Trp Tyr Cys Asp
                325                 330                 335

Asn Ala Gly Ser Val Ser Phe Phe Pro Gln Ala Glu Thr Cys Lys Val
                340                 345                 350

Gln Ser Asn Arg Val Phe Cys Asp Thr Met Asn Ser Leu Thr Leu Pro
            355                 360                 365

Ser Glu Val Asn Leu Cys Asn Val Asp Ile Phe Asn Pro Lys Tyr Asp
370                 375                 380

Cys Lys Ile Met Thr Ser Lys Thr Asp Val Ser Ser Ser Val Ile Thr
385                 390                 395                 400

Ser Leu Gly Ala Ile Val Ser Cys Tyr Gly Lys Thr Lys Cys Thr Ala
                405                 410                 415

Ser Asn Lys Asn Arg Gly Ile Ile Lys Thr Phe Ser Asn Gly Cys Asp
                420                 425                 430

Tyr Val Ser Asn Lys Gly Val Asp Thr Val Ser Val Gly Asn Thr Leu
            435                 440                 445

Tyr Tyr Val Asn Lys Gln Glu Gly Lys Ser Leu Tyr Val Lys Gly Glu
450                 455                 460

Pro Ile Ile Asn Phe Tyr Asp Pro Leu Val Phe Pro Ser Asp Glu Phe
465                 470                 475                 480

Asp Ala Ser Ile Ser Gln Val Asn Glu Lys Ile Asn Gln Ser Leu Ala
                485                 490                 495

Phe Ile Arg Lys Ser Asp Glu Leu Leu His Asn Val Asn Ala Val Lys
            500                 505                 510

Ser Thr Thr Asn Ile Met Ile Thr Thr Ile Ile Ile Val Ile Ile Val
                515                 520                 525

Ile Leu Leu Ser Leu Ile Ala Val Gly Leu Leu Leu Tyr Cys Lys Ala
530                 535                 540
```

```
Arg Ser Thr Pro Val Thr Leu Ser Lys Asp Gln Leu Ser Gly Ile Asn
545                 550                 555                 560

Asn Ile Ala Phe Ser Asn
                565
```

<210> SEQ ID NO 2
<211> LENGTH: 574
<212> TYPE: PRT
<213> ORGANISM: Artificial Sequence
<220> FEATURE:
<223> OTHER INFORMATION: Synthetic Construct

<400> SEQUENCE: 2

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Gln Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335
```

-continued

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Val Lys Ser Thr Thr Asn Ile Met Ile Thr
            515                 520                 525

Thr Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 3
<211> LENGTH: 566
<212> TYPE: PRT
<213> ORGANISM: Artificial Sequence
<220> FEATURE:
<223> OTHER INFORMATION: Synthetic Construct

<400> SEQUENCE: 3

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
            50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Lys Ala Lys Lys Glu Leu Pro
            100                 105                 110

Arg Phe Met Asn Tyr Thr Leu Asn Asn Ala Lys Lys Thr Asn Val Thr
            115                 120                 125

-continued

```
Leu Ser Lys Lys Gln Lys Gln Gln Thr Ser Ala Ile Ala Ser Gly Val
    130                 135                 140
Ala Val Cys Lys Val Leu His Leu Glu Gly Glu Val Asn Lys Ile Lys
145                 150                 155                 160
Ser Ala Leu Leu Ser Thr Asn Lys Ala Val Val Ser Leu Ser Asn Gly
                165                 170                 175
Val Ser Val Leu Thr Phe Lys Val Leu Asp Leu Lys Asn Tyr Ile Asp
            180                 185                 190
Lys Gln Leu Leu Pro Ile Leu Asn Lys Gln Ser Cys Ser Ile Ser Asn
        195                 200                 205
Ile Glu Thr Val Ile Glu Phe Gln Gln Lys Asn Asn Arg Leu Leu Glu
    210                 215                 220
Ile Thr Arg Glu Phe Ser Val Asn Ala Gly Val Thr Thr Pro Val Ser
225                 230                 235                 240
Thr Tyr Met Leu Thr Asn Ser Glu Leu Leu Ser Leu Ile Asn Asp Met
                245                 250                 255
Pro Ile Thr Asn Asp Gln Lys Lys Leu Met Ser Asn Asn Val Gln Ile
            260                 265                 270
Val Arg Gln Gln Ser Tyr Ser Ile Met Cys Ile Ile Lys Glu Glu Val
        275                 280                 285
Leu Ala Tyr Val Val Gln Leu Pro Leu Tyr Gly Val Ile Asp Thr Pro
    290                 295                 300
Cys Trp Lys Leu His Thr Ser Pro Leu Cys Thr Thr Asn Thr Lys Glu
305                 310                 315                 320
Gly Ser Asn Ile Cys Leu Thr Arg Thr Asp Arg Gly Trp Tyr Cys Asp
                325                 330                 335
Asn Ala Gly Ser Val Ser Phe Phe Pro Gln Ala Glu Thr Cys Lys Val
            340                 345                 350
Gln Ser Asn Arg Val Phe Cys Asp Thr Met Asn Ser Leu Thr Leu Pro
        355                 360                 365
Ser Glu Val Asn Leu Cys Asn Val Asp Ile Phe Asn Pro Lys Tyr Asp
    370                 375                 380
Cys Lys Ile Met Thr Ser Lys Thr Asp Val Ser Ser Ser Val Ile Thr
385                 390                 395                 400
Ser Leu Gly Ala Ile Val Ser Cys Tyr Gly Lys Thr Lys Cys Thr Ala
                405                 410                 415
Ser Asn Lys Asn Arg Gly Ile Ile Lys Thr Phe Ser Asn Gly Cys Asp
            420                 425                 430
Tyr Val Ser Asn Lys Gly Val Asp Thr Val Ser Val Gly Asn Thr Leu
        435                 440                 445
Tyr Tyr Val Asn Lys Gln Glu Gly Lys Ser Leu Tyr Val Lys Gly Glu
    450                 455                 460
Pro Ile Ile Asn Phe Tyr Asp Pro Leu Val Phe Pro Ser Asp Glu Phe
465                 470                 475                 480
Asp Ala Ser Ile Ser Gln Val Asn Glu Lys Ile Asn Gln Ser Leu Ala
                485                 490                 495
Phe Ile Arg Lys Ser Asp Glu Leu Leu His Asn Val Asn Ala Val Lys
            500                 505                 510
Ser Thr Thr Asn Ile Met Ile Thr Thr Ile Ile Ile Val Ile Ile Val
        515                 520                 525
Ile Leu Leu Ser Leu Ile Ala Val Gly Leu Leu Leu Tyr Cys Lys Ala
    530                 535                 540
```

```
Arg Ser Thr Pro Val Thr Leu Ser Lys Asp Gln Leu Ser Gly Ile Asn
545                 550                 555                 560

Asn Ile Ala Phe Ser Asn
                565
```

<210> SEQ ID NO 4
<211> LENGTH: 46
<212> TYPE: PRT
<213> ORGANISM: Artificial Sequence
<220> FEATURE:
<223> OTHER INFORMATION: Synthetic Construct

<400> SEQUENCE: 4

```
Asn Asn Arg Ala Arg Arg Glu Leu Pro Arg Phe Met Asn Tyr Thr Leu
1               5                   10                  15

Asn Asn Ala Lys Lys Thr Asn Val Thr Leu Ser Lys Lys Arg Lys Arg
            20                  25                  30

Arg Phe Leu Gly Phe Leu Leu Gly Val Gly Ser Ala Ile Ala
            35                  40                  45
```

<210> SEQ ID NO 5
<211> LENGTH: 38
<212> TYPE: PRT
<213> ORGANISM: Artificial Sequence
<220> FEATURE:
<223> OTHER INFORMATION: Synthetic Construct

<400> SEQUENCE: 5

```
Asn Asn Arg Ala Arg Arg Glu Leu Pro Arg Phe Met Asn Tyr Thr Leu
1               5                   10                  15

Asn Asn Ala Lys Lys Thr Asn Val Thr Leu Ser Lys Lys Gln Lys Gln
            20                  25                  30

Gln Thr Ser Ala Ile Ala
            35
```

<210> SEQ ID NO 6
<211> LENGTH: 38
<212> TYPE: PRT
<213> ORGANISM: Artificial Sequence
<220> FEATURE:
<223> OTHER INFORMATION: Synthetic Construct

<400> SEQUENCE: 6

```
Asn Asn Arg Lys Arg Arg Glu Leu Pro Arg Phe Met Asn Tyr Thr Leu
1               5                   10                  15

Asn Asn Ala Lys Lys Thr Asn Val Thr Leu Ser Lys Lys Gln Lys Gln
            20                  25                  30

Gln Thr Ser Ala Ile Ala
            35
```

<210> SEQ ID NO 7
<211> LENGTH: 6
<212> TYPE: PRT
<213> ORGANISM: Artificial Sequence
<220> FEATURE:
<223> OTHER INFORMATION: Synthetic Construct

<400> SEQUENCE: 7

```
Lys Lys Arg Lys Arg Arg
1               5
```

<210> SEQ ID NO 8
<211> LENGTH: 6

```
<212> TYPE: PRT
<213> ORGANISM: Artificial Sequence
<220> FEATURE:
<223> OTHER INFORMATION: Synthetic Construct

<400> SEQUENCE: 8

Lys Lys Gln Lys Gln Gln
1               5
```

RESPIRATORY SYNCYTIAL VIRUS (RSV) VACCINES

CROSS-REFERENCE TO RELATED APPLICATIONS

This application is a National Stage of International Application No. PCT/US2019/024895, filed Mar. 29, 2019, which claims benefit of U.S. Provisional Application No. 62/650,400, filed Mar. 30, 2018, which is hereby incorporated herein by reference in its entirety.

STATEMENT REGARDING FEDERALLY SPONSORED RESEARCH OR DEVELOPMENT

This invention was made with Government Support under Grant No. AI105170 and Grant No. AI093772 awarded by the National Institutes of Health. The Government has certain rights in the invention.

SEQUENCE LISTING

This application contains a sequence listing filed in electronic form as an ASCII.txt file entitled "220702-2460 Sequence Listing_ST25" created on Mar. 29, 2019. The content of the sequence listing is incorporated herein in its entirety.

BACKGROUND

Respiratory syncytial virus (RSV) is an enveloped virus with lipid membrane bilayers. RSV is a non-segmented, negative strand ribonucleic acid (RNA) genome of 15,222 nucleotides that codes for 11 messenger RNAs, each coding for a single polypeptide protein. RSV has lipid membranes that are derived from infected host cells or mammalian cell culture substrates. Three of the eleven RSV genome-encoded proteins are transmembrane surface proteins: the F (fusion), G (attachment), and SH proteins. RSV F proteins are conserved whereas RSV G proteins are variable depending on the strains. Other RSV gene products include non-structural (NS1 and NS2) proteins, and transcription regulator M2-1 and M2-2 proteins.

RSV infection occurs in seasonal outbreaks, peaking during the winter in temperate climates and during the rainy season in warmer climates. Respiratory syncytial virus (RSV) infects over 30 million people each year, and is a major cause of bronchiolitis in infants and in the elderly, resulting in 160,000 deaths annually worldwide. Patients related to RSV infections were associated with substantial morbidity, as evidenced by prolonged hospital stays, high intensive care admission rates, and high ventilatory support rates. RSV causes lower respiratory tract illness, particularly in young children and babies. Epidemiology reports suggest that RSV is also an important pathogen in adults, particularly in the elderly. Symptomatic reinfection is common throughout life and it has become increasingly apparent that RSV is an important adult pathogen as well, especially for the elderly.

Alum adjuvanted formalin-inactivated whole RSV (FI-RSV) vaccination of children resulted in vaccine enhanced disease (VED) upon the vaccinees' exposure to natural RSV infection (Kapikian A Z, M. R., et al., 1969. American journal of epidemiology 89:405-421; Kim, H. W., et al., 1969. American journal of epidemiology 89:422-434). Split virion vaccines retain immunogenic properties but have less reactogenicity than inactivated whole virus vaccines (al-Mazrou, A., et al., 1991. Cmaj 145:213-218; Cate, T. R., et al., 1977. J Infect Dis 136 Suppl:S450-455; Quinnan, G. V., et al., 1983. Rev Infect Dis 5:748-757; Wright, P. F., et al., 1983. Rev Infect Dis 5:758-764). A desirable RSV vaccine should elicit protective levels of neutralizing antibodies and avoid VED. RSV vaccines based on virus-like particles (VLP) containing virus surface proteins were shown to provide protective immune responses in preclinical animal studies (Quan, F. S., et al., 2011. J Infect Dis 204: 987-995; Lee, Y. T. et al., 2015. Int J Nanomedicine 10:4491-4505).

Vaccines are needed that are capable of achieving protection against RSV while avoiding vaccine-enhanced disease (VED).

SUMMARY

Disclosed herein are vaccines capable of achieving protection against RSV while avoiding vaccine-enhanced disease (VED). In particular, RSV vaccine constructs were molecularly designed and genetically engineered to comprise RSV pre-fusion (F) proteins displayed on the surface of a particle. In some embodiments, the RSV vaccine is a low temperature-prepared split RSV. As disclosed herein, low temperature-preparations of inactivated split RSV retain higher levels of pre-fusion F confirmation and protective immunity. In some embodiments, the RSV vaccine is a virus-like particles (VLP) engineered to display an RSV pre-F protein. For example, disclosed herein are mutant F proteins that present in a pre-fusion F conformation. Therefore, also disclosed are RSV pre-F DNA vaccines based on the disclosed pre-F mutant constructs.

In some embodiments, the RSV F protein can be expressed in a membrane-anchored form and incorporated in VLPs. Therefore, in some embodiments, the RSV F protein is a fusion protein that further comprises a membrane anchor domain, such as a transmembrane domain and optional cytoplasmic domain of a viral envelope protein.

Antigenicity tests suggest that FI-RSV and wild type F VLP vaccines display high reactivity to palivizumab and 131-2a mAb recognizing post-fusion F conformation but low or no reactivity to prefusion (pre-F) F specific 5C4 mAb. A unique F construct (F12dm-dcm) was produced, presenting both 5C4 mAb reactive pre-F epitopes and post-F epitopes (high reactivity to palivizumab and 131-2a mAb). This F12dm-dcm construct can contain mutations in the furin cleavage (e.g. sites 1 and/or 2), deletion of amino acids in the fusion peptide region, pre-F stabilizing mutations [DS-Cav1; S155C & S290C (DS), S190F & V207L (Cav1)], and a heterologous transmembrane anchor domain for anchoring on a VLP. Therefore, also disclosed herein variants of RSV F presenting pre-fusion F conformation (FIG. 1) and their use in the disclosed VLPs.

Inactivated split RSV vaccines as disclosed herein a promising RSV vaccine candidate. The newly discovered desirable properties of split RSV include: [1] higher reactivity to palivizumab (an FDA licensed monoclonal antibody drug), [2] conferring effective protective immunity with T helper type 1 (Th1)-like immune responses, [3] less likely to induce VED, and [4] more immunogenic and protective even without adjuvants compared to soluble F protein vaccines requiring adjuvants.

Low temperature-preparations of inactivated split RSV (referred to herein as "split RSV 4° C.") were developed to retain higher levels of pre-fusion F confirmation and protective immunity. RSV A2-L19F (expressing F protein of line 19F strain) was reported to retain higher levels of thermostable pre-F conformation than RSV A2 strain in previous studies (Rostad, C. A., et al., 2017. J Virol. 92(6); Stobart, C. C., et al., 2016. Nat Commun 7:13916). Replication-competent recombinant RSV A2 or A2-19F strains expressing dual F proteins might express F proteins in a pre-fusion F confirmation at higher levels.

Recombinant RSV constructs with dual F expressing RSV can be developed into a live attenuated RSV vaccine or split RSV vaccine candidate that stably express pre-F conformation. Co-expression of F-WT and F1m (furin cleavage site 2 mutation) resulted in higher levels for displaying stabilized pre-F as measured by reactivity to 5C4 pre-F specific monoclonal antibody. A bacterial artificial chromosome (BAC)-based reverse genetics technology was previously used for rescue and recovery of recombinant RSV viruses.

Recombinant RSV A2-L19F strains were produced expressing dual F proteins in a pre-F-stabilized conformation using a bacterial artificial chromosome (BAC)-based reverse genetics technology. Transcript regulator M2-2 gene deletion was shown to increase the expression of F and to attenuate the pathogenic property of RSV suggesting a live attenuated RSV vaccine (Jin, H., et al., 2000. J Virol 74:74-82; Karron, R. A., et al., 2015. Sci Transl Med 7:312ra175; Teng, M. N., et al., 2000. Journal of virology 74:9317-9321). RSV NS2 is known as a virulence gene and deletion or mutation of NS2 gene was suggested to develop live attenuated RSV vaccines.

Heterologous F (wild type)+F1m (a mutant) co-expression resulted in higher reactivity to 5C4 pre-F specific mAb. F1m is a mutated-F protein that contains furin cleavage site 2 mutation (KKRKRR (SEQ ID NO:7) to KKQKQQ (SEQ ID NO:8)) in the F protein. A dual F RSV was created that co-expressed F-WT and F1m TM by replacing the M2-2 or NS2 gene. That is, replication competent, unique recombinant viruses of RSV A2-L19F were generated for dual expression of F proteins where RSV NS2 virulence gene or M2-2 gene was replaced with F in the RSV A2-L19F backbone.

As for alternative approaches to retain high production titers of RSV with increased levels of pre-fusion F proteins, Vero cells that stably express F (wild type) or F1m (mutant) were generated and used as an RSV vaccine manufacturing substrate cell line. Generation of RSV A2-L19F expressing dual F proteins where M2-2 or NS2 was replaced with F and tested in an inactivated, split RSV 4° C. vaccine platform.

Inclusion of RSV F encoding DNA vaccines in the RSV vaccination (split RSV, F VLP) was found to improve the efficacy of RSV vaccination while avoiding VED.

Also disclosed are combinations of the disclosed vaccines. In some embodiments, the disclosed VLP comprising an RSV F protein, e.g. pre-fusion F protein, can enhance the efficacy of RSV split vaccine, e.g. without the need for a separate adjuvant. Therefore, in some embodiments, the disclosed vaccine compositions can also contain, or be co-administered with, at least one RSV split vaccine. For example, one combination is a low temperature-preparations of inactivated split RSV with an RSV VLP displaying F, pre-F, or a combination thereof. Another combination is a low temperature-preparations of inactivated split RSV with an RSV F DNA vaccine, RSV pre-F DNA vaccine, or a combination thereof.

Also disclosed is an adjuvant that can enhance vaccine efficacy while preventing VED. In particular, a unique combination of low dose Toll-like receptor 4 (TLR4) agonist and low dose TLR9 agonist can be used in combination with any vaccine, such as a vaccine for influenza, RSV, and other protein subunit vaccines. In particular embodiments, the vaccine can be a split RSV vaccine, RSV F protein vaccine, split influenza virus, or the disclosed RSV F VLP vaccines.

In some embodiments, the TLR4 agonist is 3-O-desacyl-4'-monophosphoryl lipid A (MPL). In some embodiments, the TLR9 against is a CpG oligodeoxynucleotide. In some embodiments, the TLR9 against is a heat-killed lactic acid bacteria (DK128), a cell wall skeleton (CWS) of Bacillus Calmette-Guérin (BCG), or any combination thereof.

In some embodiments, a "low dose" is a 5- to 50-fold lower dose ranges than standard doses. For example, F protein only and alum adjuvant vaccinated mice show severe histopathology, whereas the disclosed low dose CpG+MPL adjuvanted RSV F protein or split RSV vaccinated mice displayed no lung histopathology. In some embodiments, a low dose of MPL can be 0.5-100 µg/kg, such as 1-10 µg/kg. In some embodiments, a low dose of CpG can be 1-100 µg/kg, such as 2-40 µg/kg.

Also disclosed are isolated polynucleotides encoding the disclosed RSV F proteins and cells containing these polynucleotides.

Also disclosed are methods of vaccinating a subject for RSV by administering to a subject in need thereof a composition comprising a vaccine disclosed herein. The disclosed vaccine may be administered alone or in combination with one or more additional RSV vaccines.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2B shows RSV neutralizing activity of sera from mice that were immunized with 5 µg of F VLPs (n=5). RSV A2-K-L19F expressing red Katushka 2 protein (500 PFU/Vero cells).

FIG. 3C shows lung histopathology. Naïve Infection: naïve mice with RSV challenge. Adult BALB/c mice with a single dose (5 µg) of FI-RSV or split RSV without adjuvants and then RSV (1×10$^6$ PFU) challenge. (Bars: 100 µm).

FIGS. 7A to 7D show F VLP confers protection against RSV without VED in adult mice based on body weight (BW) changes (FIG. 7A), RSV neutralizing titers (FIG. 7B), RSV titers [PFU/g lung tissues] (FIG. 7C), and lung histopathology (FIG. 7D). Scores in adult mice (n=5) after RSV challenge. N: naïve, VLP: F VLP (10 μg), RSV: live RSV (1×104 PFU). FI: FI-RSV (5 μg).

Figure 9B:
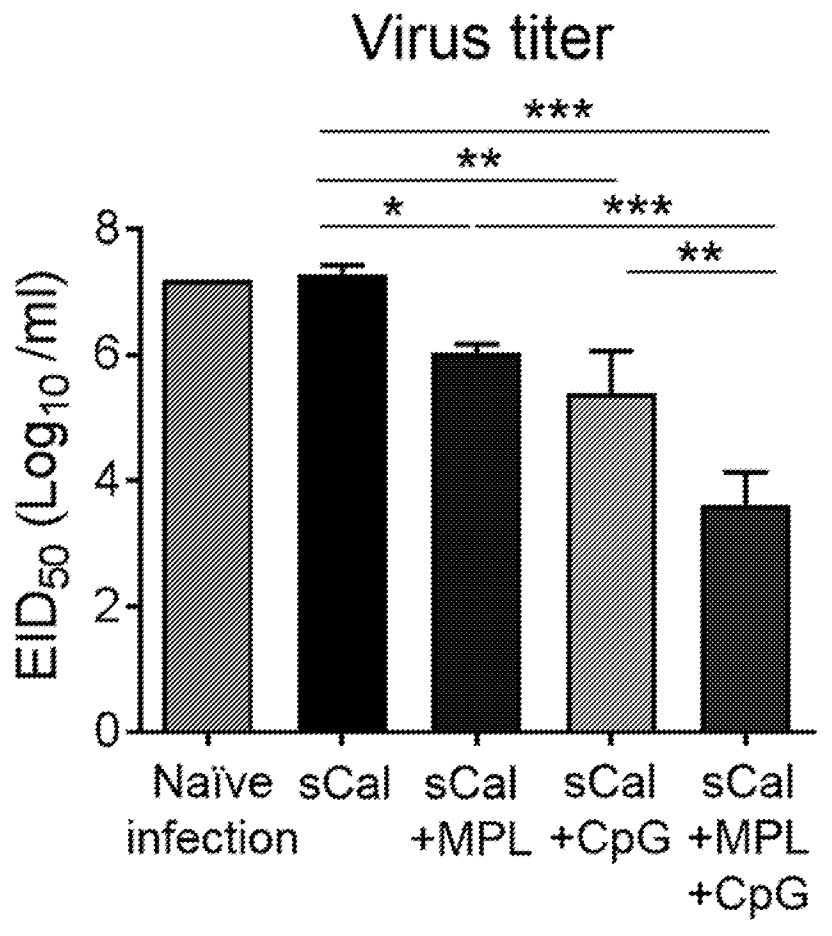

FIGS. 9A and 9B show protective efficacy of the immunized mice with sCal vaccine (2009 H1N1 pandemic virus split influenza vaccine) plus MPL+CpG combination adjuvant. 4 weeks after boost immunization, the immunized mice were infected with 0.5×LD50 of rgH5N1 virus. FIG. 9A (left panel) shows body weight (BW) changes monitored for 7 days after infection. The right panel of FIG. 9A shows enhanced pause (PenH) of respiration measured by plethysmography. Percentages of changes were based on the value in day 0. FIG. 9B shows lung viral titers at day 7 post infection. Virus titration was determined by using embryonated chicken eggs and presented in 50% egg infectious titers ($EID_{50}$). All data were shown in mean±SEM. For statistical analysis, One-way ANOVA and Tukey's post-multiple comparison test were performed. *; 0.033, ; p<0.002, and *; p<0.001 between the indicated groups.

FIG. 10A shows the modified full-length RSV F genes in VLP, furin protease cleavages (furin 2, furin 1, black arrowheads) generate F1 and F2 subunit fragments in wild type (WT) F-TM. F-dcmTM (DS-Cav1): A full-length F contains DS-Cav1 mutations known to stabilize pre-F conformation in soluble proteins with foldon, DS-Cav1 mutations of S155C, S190F, V207L, and S290C. F1d-dcmTM: mutation in furin site 1, FP deletion, and DS-Cav1. F12d-dcmTM: mutation in furin sites 1 and 2, FP deletion, and DS-Cav1. FIG. 10B shows WT (SEQ ID NO:4) and modified amino acid sequences in RSV F furin cleavage sites and fusion domain, RSV F furin cleavage site F1d-dcmTM (SEQ ID NO:5) and F12d-dcmTM (SEQ ID NO:6) constructs have a deletion of the fusion peptide (FP) and furin 1 cleavage mutation (F1d-dcmTM) or both furin 1 and 2 cleavage mutations (F12d-dcmTM). p27, excised peptide; FP, fusion peptide; HRA, —B, and -C heptad repeats A, B, and C are indicated; TM, RSV F protein transmembrane domain including a C-terminal tail.

FIG. 11A shows D25 mAb specific for pre-F site Ø epitope. FIG. 11B shows 5C4 mAb specific for pre-F site Ø epitope, F mutant VLPs (0.25 μg/50 μL) were coated on 96-well plates, then 5C4 mAb were used to capture in serial dilution. FIG. 11C shows palivizumab specific for the F site II epitope. FIG. 11D shows 131-2a mAb specific for post-F site I. FIG. 11E shows AM14 mAb specific for the F site V epitope. Each figure displays data that reproducibly represents at least triple repeat experiments. The serial dilution of M1 VLP (influenza virus matrix 1 (M1) core protein) and PBST buffer only were used as control.

DETAILED DESCRIPTION

Figure 1:
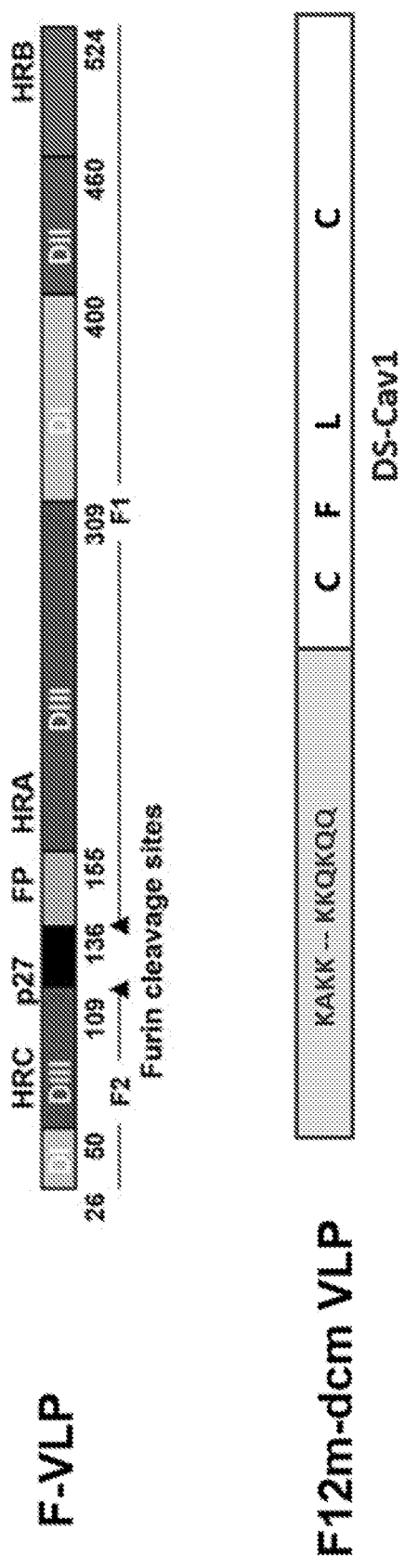
FIG. 1 is an illustration of a F-VLP and an embodiment of a disclosed Pre-F VLP (F12dm-dcm).

A vaccine against RSV is currently not available, but is desired due to the high disease burden. A safe and effective RSV vaccine should induce RSV neutralizing (NA) antibodies, control lung viral titers below the detection limit, and avoid RSV VED (no VED-prone T helper type 2 (Th2) responses). Disclosed are vaccines capable of achieving protection against RSV while avoiding vaccine-enhanced disease (VED).

Definitions

It must be noted that as used herein and in the appended claims, the singular forms "a," "an," and "the" include plural referents unless the context clearly dictates otherwise. Thus, for example, reference to "a peptide" includes a plurality of such peptides, reference to "the peptide" is a reference to one or more peptides and equivalents thereof known to those skilled in the art, and so forth.

In this specification and in the claims that follow, reference will be made to a number of terms that shall be defined to have the following meanings:

"Optional" or "optionally" means that the subsequently described event or circumstance can or cannot occur, and that the description includes instances where the event or circumstance occurs and instances where it does not. For example, the phrase "optionally a signal peptide" means that the signal peptide may or may not be included. As used herein the term "adjuvant" refers to a compound that, when used in combination with a specific immunogen (e.g. a VLP) in a formulation, will augment or otherwise alter or modify the resultant immune response. Modification of the immune response includes intensification or broadening the specificity of either or both antibody and cellular immune responses. Modification of the immune response can also mean decreasing or suppressing certain antigen-specific immune responses.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

As used herein an "effective amount" or "effective dose" generally refers to that amount of the disclosed VLPs sufficient to induce immunity, to prevent and/or ameliorate an infection or to reduce at least one symptom of an infection and/or to enhance the efficacy of another dose of a VLP. An effective dose may refer to the amount of VLPs sufficient to delay or minimize the onset of an infection. An effective dose may also refer to the amount of VLPs that provides a therapeutic benefit in the treatment or management of an infection. Further, an effective dose is the amount with respect to VLPs of the invention alone, or in combination with other therapies, that provides a therapeutic benefit in the treatment or management of an infection. An effective dose may also be the amount sufficient to enhance a subject's (e.g., a human's) own immune response against a subsequent exposure to an infectious agent. Levels of immunity can be monitored, e.g., by measuring amounts of neutralizing secretory and/or serum antibodies, e.g., by plaque neutralization, complement fixation, enzyme-linked immunosorbent, or microneutralization assay. In the case of a vaccine, an "effective dose" is one that prevents disease and/or reduces the severity of symptoms.

The term "fusion protein" in some instances refers to a viral surface glycoproteins (a.k.a "F protein") that mediate virus entry to the target cells via fusion between virus and target cell membranes. Antibodies binding to the RSV fusion proteins are known to neutralize the virus and block the virus entry to the target cells, thereby preventing the viral infection. The term "fusion protein" in other instances refers to a chimeric polypeptide formed by the joining of two or more polypeptides through a peptide bond formed between the amino terminus of one polypeptide and the carboxyl terminus of another polypeptide. The fusion protein can be expressed as a single polypeptide from nucleic acid sequence encoding the single contiguous fusion protein.

As used herein the term "immune stimulator" refers to a compound that enhances an immune response. These molecules comprise various cytokines, and chemokines with immunostimulatory, and pro-inflammatory activities, such as vaccine adjuvants, interferons, interleukins; growth factors (e.g., granulocyte-macrophage (GM)-colony stimulating factor (CSF)); and other immunostimulatory molecules. The immune stimulator molecules can be administered in the same formulation as the disclosed split RSV and VLPs, or can be administered separately.

The term "nucleic acid" refers to a natural or synthetic molecule comprising two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The terms "peptide," "protein," and "polypeptide" are used interchangeably to refer to a natural or synthetic molecule comprising two or more amino acids linked by the carboxyl group of one amino acid to the alpha amino group of another.

The term "protein domain" refers to a portion of a protein, portions of a protein, or an entire protein showing structural integrity; this determination may be based on amino acid composition of a portion of a protein, portions of a protein, or the entire protein.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

As used herein the term "protective immune response" or "protective response" refers to an immune response mediated by antibodies against an infectious agent, which is exhibited by a vertebrate (e.g., a human), that prevents or ameliorates an RSV infection or reduces at least one symptom thereof. The disclosed vaccines can stimulate the production of antibodies that, for example, neutralize infectious agents, blocks infectious agents from entering cells, blocks replication of said infectious agents, and/or protect host cells from infection and destruction. The term can also refer to an immune response that is mediated by T-lymphocytes and/or other white blood cells against an infectious agent, exhibited by a vertebrate (e.g., a human), that prevents or ameliorates RSV infection or reduces at least one symptom thereof.

The term "split" refers to splitting the enveloped virus particles. Current influenza vaccines are a platform of inactivated split influenza virus particles. Preparations of split RSV vaccines involve the process of inactivation of RSV by using formaldehyde. Inactivated RSV particles are further treated with detergents such as Triton X-100 to split the inactivated RSV. After dialysis to remove detergents and formalin, split RSV vaccines are prepared.

The term "subject" refers to any individual who is the target of administration, treatment, or vaccination. The subject can be a vertebrate, for example, a mammal. Thus, the subject can be a human or veterinary patient. The term "patient" refers to a subject under the treatment of a clinician, e.g., physician. All ages of subjects are intended to be covered. In particular, infants and young children are appropriate subjects or patients for a RSV vaccine.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "vaccine" refers to a formulation, e.g. containing a disclosed VLP, which is in a form that is capable of being administered to a vertebrate and which induces a protective immune response sufficient to induce immunity to prevent and/or ameliorate an infection and/or to reduce at least one symptom of an infection. Typically, the vaccine comprises a conventional saline or buffered aqueous solution medium, e.g. in which the disclosed VLPs are suspended or dissolved. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses.

The term "virus-like particle" (VLP) refers to a structure that in at least one attribute resembles a virus but which has not been demonstrated to be infectious. Virus-like particles do not carry genetic information encoding for the proteins of the virus-like particles. In general, virus-like particles lack a viral genome and, therefore, are noninfectious. In addition, virus-like particles can often be produced in large quantities by heterologous expression and can be easily purified.

RSV F VLP Constructs

The RSV fusion glycoprotein (RSV F) is an attractive vaccine antigen, since it is the principal target of RSV neutralizing antibodies in human sera. A neutralizing monoclonal antibody against RSV F (palivizumab) can prevent severe disease and has been approved for prophylaxis in preterm infants. RSV F fuses the viral and host cell membranes by irreversible protein refolding from the labile pre-fusion conformation to the stable post-fusion conformation. Structures of both conformations have been determined for RSV F.

The RSV F protein directs penetration of RSV by fusion between the virion's envelope protein and the host cell plasma membrane. Later in infection, the F protein expressed on the cell surface can mediate fusion with neighboring cells to form syncytia. The F protein is a type I transmembrane surface protein that has an N-terminal cleaved signal peptide and a membrane anchor near the C-terminus. RSV F is synthesized as an inactive F0 precursor that assembles into a homotrimer and is activated by cleavage in the trans-Golgi complex by a cellular endoprotease to yield two disulfide-linked subunits. The N-terminus of the F1 subunit that is created by cleavage contains a hydrophobic domain (the fusion peptide) that inserts directly into the target membrane to initiate fusion. The F1 subunit also contains heptad repeats that associate during fusion, driving a conformational shift that brings the viral and cellular membranes into close proximity.

Since RSV infection can be prevented by providing neutralizing antibodies to a vertebrate, a vaccine comprising RSV F proteins may induce, when administered to a vertebrate, neutralizing antibodies in vivo. Thus, disclosed herein are RSV F VLPs that can be formulated into vaccines or antigenic formulations for protecting vertebrates (e.g. humans) against RSV infection or at least one symptom thereof. Also disclosed are vectors that when transfected into host cells, will produce virus like particles (VLPs) comprising RSV F proteins. In some embodiments, RSV F VLPs may include at least a viral core protein (e.g. influenza M1 protein) and at least one F protein in either RSV pre-fusion or post-fusion conformation.

Immunization with post-fusion F (post-F) proteins, which present the antigenic sites (I, II, IV), induces neutralizing antibodies clearing lung viral replication in mice and cotton rats after challenge (Hwang, H. S., et al., 2014. Antiviral Res 110C:115-123; Hwang, H. S., et al., 2017. Virology 511: 142-151; Hwang, H. S., et al., 2016. Virology 494:215-224; Raghunandan, R., et al., 2014. Vaccine 32:6485-6492; Schneider-Ohrum, K., et al., 2017. J Virol 91; Smith, G., et al., 2012. PloS one 7:e50852; Swanson, K. A., et al., 2011. Proc Natl Acad Sci USA 108:9619-9624).

The results of antigenicity tests (concentration at 0.05 µg/well, Table 1) suggest that RSV vaccines [F VLP (F-WT or wild type F VLP), FI-RSV, or split RSV] with post-F protein display high reactivity to palivizumab (site II) and 131-2a (site I) antibodies, but low reactivity to prefusion F (pre-F) specific 5C4 monoclonal antibody (mAb). A preferred F protein for use in the disclosed VLPs should be reactive to both 5C4 mAb (pre-F) and palivizumab (post-F).

Therefore, disclosed herein is a recombinant RSV F protein that is stabilized in a pre-F conformation for use in the disclosed vaccine compositions. Pre-F conformation stabilizing mutations are known in the art, and are described in McLellan, J. S., 2015. Curr Opin Virol 11:70-75, and McLellan, J. S., et al., 2013. Science 342:592-598, which are incorporated by reference in their entireties for the teaching of these mutations. Examples of conformation stabilizing mutations include mutation selected from the group comprising S155C, S290C, S190F, V207L, and any combination thereof.

In some embodiments to further stabilize the pre-fusion conformation of F on VLP platforms, the disclosed recombinant RSV F protein has additional mutations in the furin cleave sites 1 and 2. For example, the furin cleavage site 2 mutation can be an arginine to glutamine substitution at amino acids 131-136 (i.e., KKRKRR (SEQ ID NO:7) to KKQKQQ (SEQ ID NO:8)). The furin cleavage site 1 mutation can be a 106-109 (KAKK).

In some embodiments, the disclosed recombinant RSV F protein has an additional mutation in the fusion peptide region for stabilizing the pre-fusion conformation of F on VLP platforms. For example, the protein can have a deletion of at least 1, 2, 3, 4, 5, 6, 7, 8, 9, or 10 amino acids in the fusion peptide region between the amino acid residues 138-147.

The F protein can be derived from any available strain of RSV, such as A2, L19F, or DB1 (Rostad, C. A., et al., 2017. J Virol. 92(6); Stobart, C. C., et al., 2016. Nat Commun 7:13916). In some cases, the VLP comprises F proteins from more than one strain of RSV, e.g. a dual F protein. In some embodiments, the VLP comprises F proteins from both A2 and L19F strains. In some cases, one or both of these F proteins are in a pre-fusion F conformation.

Therefore, in some embodiments, the RSV F comprises an amino acid sequence that is at least 85%, 90%, 95%, 96%, 97%, 98% 99%, or 100% identical to MELLILKANAITTILTAVTFCFASGQNITEEFYQSTCSAVSKGYLSALRTGWYTSV ITIELSNIKKNKCNGTDAKIKLIKQELDKYKNAVTELQLLMQSTPATNNKAKKELP RFMNYTLNNAKKTNVTLSKKQKQQTSAIASGVAVCKVLHLEGEVNKIKSALLST NKAVVSLSNGVSVLTFKVLDLKNYIDKQLLPILNKQSCSISNIETVIEFQQKNNRL LEITREFSVNAGVTTPVSTYMLTNSELLSLINDMPITNDQKKLMSNNVQIVRQQS YSIMCIIKEEVLAYVVQLPLYGVIDTPCWKLHTSPLCTTNTKEGSNICLTRTDRG WYCDNAGSVSFFPQAETCKVQSNRVFCDTMNSLTLPSEVNLCNVDIFNPKYDC KIMTSKTDVSSSVITSLGAIVSCYGKTKCTASNKNRGIIKTFSNGCDYVSNKGVD TVSVGNTLYYVNKQEGKSLYVKGEPIINFYDPLVFPSDEFDASISQVNEKINQSL AFIRKSDELLHNVNAVKSTTNIMITTIIIVIIVILLSLIAVGLLLYCKARSTPVTLSKDQ LSGINNIAFSN (F1-WT, SEQ ID NO:1), or an immunogenic fragment thereof.

Therefore, in some embodiments, the RSV F comprises an amino acid sequence that is at least 85%, 90%, 95%, 96%, 97%, 98% 99%, or 100% identical to MELLILKANAITTILTAVTFCFASGQNITEEFYQSTCSAVSKGYLSALRTGWYTSV ITIELSNIKKNKCNGTDAKIKLIKQELDKYKNAVTELQLLMQSTPATNNRARRELP RFMNYTLNNAKKTNVTLS KKQKQQFLGFLLGVGSAIASGVAVSKVLHLEGEVNK IKSALLSTNKAVVSLSNGVSVLTSKVLDLKNYIDKQLLPIVNKQSCSISNIETVIEF QQKNNRLLEITREFSVNAGVTTPVSTYMLTNSELLSLINDMPITNDQKKLMSNNV QIVRQQSYSIMSIIKEEVLAYVVQLPLYGVIDTPCWKLHTSPLCTTNTKEGSNICL TRTDRGWYCDNAGSVSFFPQAETCKVQSNRVFCDTMNSLTLP- SEVNLCNVDIF NPKYDCKIMTSKTDVSSSVITSL-GAIVSCYGKTKCTASNKNRGIIKTFSNGCDYV SNKGVDTVSVGNTLYYVNKQEGKSLYVKGEPI-INFYDPLVFPSDEFDASISQVN EKINQSLAFIRKS-DELLHNVNAVKSTTNIMITTIIIVIIVILLSLIAVGLLLY-CKARSTPV TLSKDQLSGINNIAFSN (F1 mTM, SEQ ID NO:2), or an immunogenic fragment thereof.

Therefore, in some embodiments, the RSV F comprises an amino acid sequence that is at least 85%, 90%, 95%, 96%, 97%, 98% 99%, or 100% identical to MELLILKA-NAITTILTAVTFCFASGQNITEEFYQSTCSAVSKGYL-SALRTGWYTSV ITIELSNIKKNKCNGTDAKIK-LIKQELDKYKNAVTELQLLMQSTPATNNKAKKELP RFMNYTLNNAKKTNVTL<u>SKKQKQQ[T]</u>SAIASGVAV <u>CK</u>VLHLEGEVNKIKSALLST NKAVVSLSNGVSVLT F<u>K</u>VLDLKNYIDKQLLPI <u>L</u>NKQSCSISNIETVIEFQQKNNRL LEITRE-FSVNAGVTTPVSTYMLTN-SELLSLINDMPITNDQKKLMSNNVQIVRQQS YSIM <u>C</u>IIKEEVLAYVVQLPLYGVIDTPCWKLHTSPLCTTNT-KEGSNICLTRTDRG WYCD-NAGSVSFFPQAETCKVQSNRVFCDTMNSLTLP-SEVNLCNVDIFNPKYDC KIMTSKTDVSSSVITSL-GAIVSCYGKTKCTASNKNRGIIKTFSNGCDYVSNKG-VD TVSVGNTLYYVNKQEGKSLYVKGEPI-INFYDPLVFPSDEFDASISQVNEKINQSL AFIRKS-DELLHNVNAVKSTTNIMITTIIIVIIVILLSLIAVGLLLY-CKARSTPVTLSKDQ LSGINNIAFSN (F12dm-dcmTMrsv, SEQ ID NO:3), or an immunogenic fragment thereof. Mutated amino acids are underlined and the residyu replacing the deleted amino acids is bracketed.

To anchor multiple copies of one RSV pre-fusion F protein on the surface of a particle, the one RSV pre-fusion F protein may be expressed in a membrane-anchored form and incorporated in virus-like particles (VLPs). Therefore, in some embodiments, the disclosed RSV pre-fusion F protein further comprises a membrane anchor domain, such as a transmembrane domain and optional cytoplasmic domain of a viral envelope protein.

In some embodiments, the membrane anchor domain comprises the full HA protein sequence.

Also disclosed are polynucleotides comprising nucleic acid sequences encoding the disclosed RSV pre-fusion F proteins. For example, the nucleic acid sequences can be operably linked to expression control sequences. Thus, also disclosed are expression vectors for producing the disclosed proteins as well as cells containing these polynucleotides and vectors for replicating the polynucleotides and vectors or to produce the disclose proteins and/or VLPs. Therefore, the disclosed cell can also contain nucleic acid sequences encoding an M1 protein, including a vector comprising the nucleic acid sequences encoding an M1 protein.

Also disclosed is a dual vector comprising a first nucleic acid sequence encoding the disclosed RSV pre-fusion F protein and a second nucleic acid sequence encoding an influenza M1 protein.

In some embodiments, the nucleic acid sequence encoding the disclosed RSV pre-fusion F protein is operably linked to a first expression control sequence; and the nucleic acid sequence encoding an M1 protein is operably linked to a second expression control sequence.

The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked DNA polynucleotide. In many, but not all, common embodiments, the vectors of the present invention are plasmids or bacmids.

Thus, also disclosed are nucleotides that encode proteins, including chimeric molecules, cloned into an expression vector that can be expressed in a cell that induces the formation of VLPs. An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. In one embodiment, said nucleotides encode for an RSV F protein (as discussed above). In some embodiments, the expression vector is a baculovirus vector.

In addition, the nucleotides can be sequenced to ensure that the correct coding regions were cloned and do not contain any unwanted mutations. The nucleotides can be subcloned into an expression vector (e.g. baculovirus) for expression in any cell. The above is only one example of how the RSV viral proteins can be cloned. Suitable vectors can be routinely selected based on the choice of cell used to produce the VLP. For example, where insect cells are used, suitable vectors include baculoviruses.

Also disclosed are vectors that comprise RSV nucleotides disclosed herein. The vector may be, for example, a phage, plasmid, viral, or retroviral vector. The vectors comprise RSV genes operatively linked to an appropriate promoter, such as the AcMNPV polyhedrin promoter (or other baculovirus). The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Expression vectors can include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus). Other vectors that can be used include vectors for use in bacteria.

Among eukaryotic host cells are yeast, insect, avian, and mammalian host cells. Non limiting examples of insect cells are, *Spodoptera frugiperda* (Sf) cells, e.g. Sf9, Sf21, *Trichoplusia ni* cells, e.g. High Five cells, and *Drosophila* S2 cells. Examples of mammalian cells are COS cells, baby hamster kidney cells, mouse L cells, LNCaP cells, Chinese hamster ovary (CHO) cells, human embryonic kidney (HEK) cells, and African green monkey cells, CV1 cells, HeLa cells, MDCK cells, Vero and Hep-2 cells. *Xenopus laevis* oocytes, or other cells of amphibian origin, may also be used. Prokaryotic host cells include bacterial cells, for example, *E. coli, B. subtilis*, and mycobacteria.

Virus-Like Particles (VLPs)

Influenza VLP vaccines that were produced in insect cells were proven to be safe and efficacious in clinical trials (Glenn, G. M., et al., 2013. Vaccine 31:524-532; Khurana, S., et al., 2011. Journal of virology 85:10945-10954; Lopez-Macias, C., et al., 2011. Vaccine 29:7826-7834). RSV pre-fusion F protein may be expressed on the surface of a particle to mimic the natural conformation of RSV pre-fusion F protein on influenza virus M1 matrix VLPs. For example, the disclosed RSV pre-fusion F proteins were incorporated into virus-like particles (VLPs) by including within the RSV pre-fusion F protein a membrane anchor domain, such as a transmembrane domain and optional cytoplasmic domain of a viral envelope protein.

Non-replicating VLPs resemble infectious virus particles in structure and morphology, and contain immunologically relevant viral structural proteins. VLPs have been produced from both non-enveloped and enveloped viruses. Envelopes of VLPs are derived from the host cells similar to the way as enveloped viruses such as influenza A virus obtain their lipid envelopes from their host cells. Therefore, membrane-anchored proteins on the surfaces of enveloped viruses will be expressed in a native-like conformation if they are expressed in a membrane-anchored form.

VLPs can be harvested approximately 48 to 96 hours post infection, when the levels of VLPs in the cell culture medium are near the maximum but before extensive cell lysis. The Sf9 cell density and viability at the time of harvest can be about $0.5 \times 10^6$ cells/ml to about $1.5 \times 10^6$ cells/ml with at least 20% viability, as shown by dye exclusion assay. Next, the medium can be removed and clarified. NaCl can be added to the medium to a concentration of about 0.4 to about 1.0 M, preferably to about 0.5 M, to avoid VLP aggregation. The removal of cell and cellular debris from the cell culture medium containing VLPs can be accomplished by tangential flow filtration (TFF) with a single use, pre-sterilized hollow fiber 0.5 or 1.00 µm filter cartridge or a similar device.

Next, VLPs in the clarified culture medium can be concentrated by ultrafiltration using a disposable, pre-sterilized 500,000 molecular weight cut off hollow fiber cartridge. The concentrated VLPs can be diafiltrated against 10 volumes pH 7.0 to 8.0 phosphate-buffered saline (PBS) containing 0.5 M NaCl to remove residual medium components.

The concentrated, diafiltered VLPs can be furthered purified on a 20% to 60% discontinuous sucrose gradient in pH 7.2 PBS buffer with 0.5 M NaCl by centrifugation at 6,500×g for 18 hours at about 4° C. to about 10° C. Usually VLPs will form a distinctive visible band between about 30% to about 40% sucrose or at the interface (in a 20% and 60% step gradient) that can be collected from the gradient and stored. This product can be diluted to comprise 200 mM of NaCl in preparation for the next step in the purification process. This product contains VLPs and may contain intact baculovirus particles.

Further purification of VLPs can be achieved by anion exchange chromatography, or 44% isopycnic sucrose cushion centrifugation. In anion exchange chromatography, the sample from the sucrose gradient (see above) is loaded into column containing a medium with an anion (e.g. Matrix Fractogel EMD TMAE) and eluded via a salt gradient (from about 0.2 M to about 1.0 M of NaCl) that can separate the VLP from other contaminates (e.g. baculovirus and DNA/RNA). In the sucrose cushion method, the sample comprising the VLPs is added to a 44% sucrose cushion and centrifuged for about 18 hours at 30,000 g. VLPs form a band at the top of 44% sucrose, while baculovirus precipitates at the bottom and other contaminating proteins stay in the 0% sucrose layer at the top. The VLP peak or band is collected.

The intact baculovirus can be inactivated, if desired. Inactivation can be accomplished by chemical methods, for example, formalin or β-propiolactone (BPL). Removal and/or inactivation of intact baculovirus can also be largely accomplished by using selective precipitation and chromatographic methods known in the art, as exemplified above. Methods of inactivation can comprise incubating the sample containing the VLPs in 0.2% of BPL for 3 hours at about 25° C. to about 27° C. The baculovirus can also be inactivated by incubating the sample containing the VLPs at 0.05% BPL at 4° C. for 3 days, then at 37° C. for one hour.

After the inactivation/removal step, the product comprising VLPs can be run through another diafiltration step to remove any reagent from the inactivation step and/or any residual sucrose, and to place the VLPs into the desired buffer (e.g. PBS). The solution comprising VLPs can be sterilized by methods known in the art (e.g. sterile filtration) and stored in the refrigerator or freezer.

Split Enveloped Virus Vaccines

The enveloped RSV virus can be produced by replication on a suitable cell substrate, in serum or in a serum free process. Tissue culture-grown RSV may be produced in Hep2, BHK2, or Vero cells. Some of the disclosed vaccine formulations involve enveloped viruses that are capable of being split. The enveloped virus of RSV and influenza virus may be derived from a wide variety of sources including viruses from human or animal origin. The disclosed vaccine optionally comprises split virus selected from the group consisting of RSV and influenza virus.

The splitting of the virus means a treatment for disrupting or fragmenting whole virus, infectious (wild-type or attenuated) or non-infectious or inactivated virus. A disrupting and splitting agent is generally, but not necessarily, a surfactant. The virus to be split may be a chimeric or recombinant virus, having pre-fusion F immunogenic elements. The splitting treatment results in a full or partial fragmentation of the virus lipid bilayer envelop components and proteins which alters the antigenicity and immunogenicity.

Split virus can be prepared by contacting the inactivated or live RSV or influenza virus with a splitting agent to fully or partially disrupt the viral envelope lipid bilayers. Inactivation of the enveloped virus with cross-linking chemicals such as formalin may stabilize the viral protein antigens. Some viral proteins upon splitting the enveloped virus may become fully or partially exposed, possibly resulting in enhancing the antigenicity and immunogenicity. The loss of lipid membrane integrity of the enveloped virus after splitting as well as formalin inactivation renders the virus non-infectious as assessed by suitable in vitro titration assays. Once disrupted, the viral envelope proteins may retain or enhance antigenicity or immunogenicity although viral proteins are no longer associated with infecting target host cells.

The process for the preparation of the split enveloped virus may further include filtration and/or other separation steps such as ultracentrifugation, ultrafiltration, and zonal centrifugation. Prior and optional processes involve an inactivation step e.g. with formaldehyde or 3-propiolactone or UV treatment which may be carried out before or after splitting.

The inactivated split vaccines are the most common platform of seasonal influenza vaccination. The split RSV vaccines may contain membrane fragments and membrane envelope proteins as well as non-membrane proteins such as viral matrix protein and nucleoprotein but are not capable of replication. Split vaccines will contain most of the virus structural proteins but not necessarily in the same proportions as in the whole virus. Preferred split virus preparations comprise most of viral structural proteins. Subunit vaccines on the other hand consist of one or a few highly purified proteins. For example an RSV subunit vaccine could contain purified viral surface fusion proteins known to be capable of eliciting RSV neutralizing antibodies upon vaccination.

Various splitting agents such as non-ionic and ionic surfactants as well as various other reagents may be used. A preferred splitting agent is non-ionic surfactant triton X-100 (t-octylphenoxypolyethoxyethanol). Preferably, the final concentration of stabilizing surfactant triton X-100 present in the final vaccine formulation is between 0.01 to 5%, more preferably 0.05 to 2%. The most preferable range is between 0.1 to 1% triton X-100 in splitting RSV and in preparing split RSV vaccines.

Vaccine Compositions

Disclosed herein are vaccine compositions that comprise one or more of the RSV pre-fusion F proteins on VLP and or spit RSV vaccines described above. Although not required, the vaccine compositions optionally contain one or more immunostimulants. An immunostimulant refers to essentially any substance that enhances or potentiates an immune response (antibody or cell-mediated) to an exogenous antigen. One preferred type of immunostimulant is an adjuvant.

In some embodiments, the adjuvant is combination of low dose TLR4 agonist and low dose TLR9. In some embodiments, the TLR4 agonist is 3-O-desacyl-4'-monophosphoryl lipid A (MPL). In some embodiments, the TLR9 against is a CpG oligodeoxynucleotide. In some embodiments, a low dose of MPL can be 0.5-1 µg. In some embodiments, a low dose of CpG can be 2-4 µg.

Figure 5A:
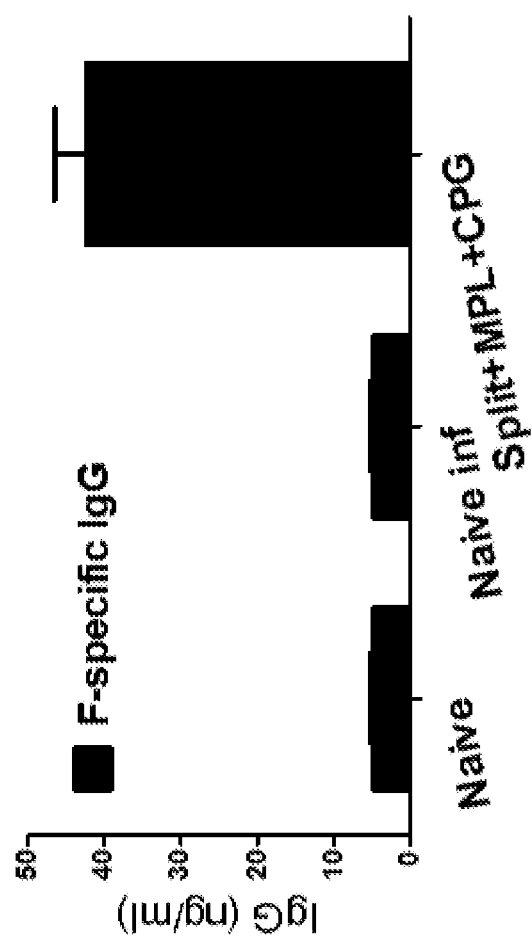
FIGS. 5A and 5B show CpG+MPL adjuvant effects on lung histopathology in 2 weeks (2W) old infant (n=12, both sexes) primed mice, at day 5 post RSV challenge (1×10$^6$ PFU). FI-RSV (5 µg) only, Split RSV (5 µg) only, Split (5 µg)+CpG (4 µg)+MPL (1 µg). (Bars: 100 µm)
Figure 5B:
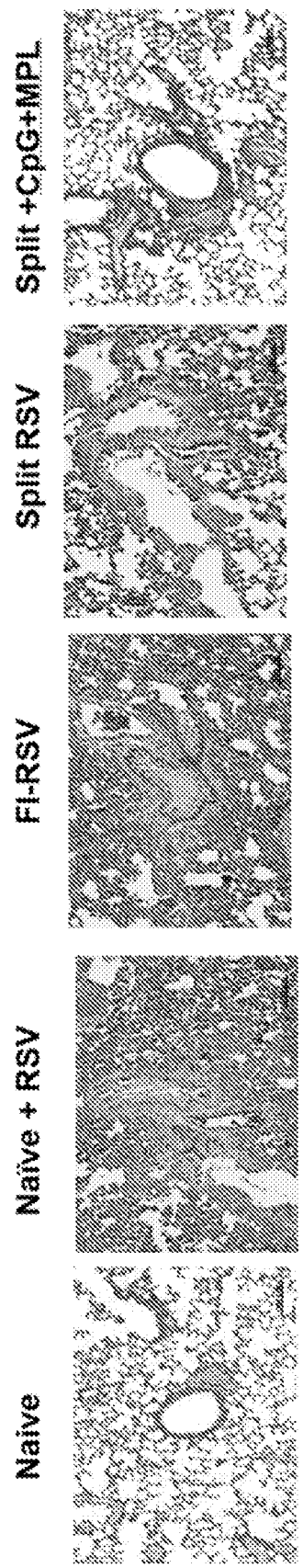

CpG adjuvant with unmethylated CpG motifs is recognized by TLR 9 and induces Th1 immune responses. As disclosed herein, the combination of low dose CpG (e.g. 4 µg) and MPL (e.g. 1 µg) obviates RSV F protein vaccine-enhanced lung histopathology (FIG. 5).

Many adjuvants contain a substance designed to protect the antigen from rapid catabolism, such as aluminum hydroxide, and a stimulator of immune responses, such as heat-killed lactic acid bacteria, cell-wall skeleton of BCG vaccines, or *Mycobacterium tuberculosis* derived proteins. The adjuvant may be a submicron oil-in-water emulsion agent. For example, the adjuvant may comprise MF59™, which is a sub-micron oil-in-water emulsion of a squalene, polyoxyethylene sorbitan monooleate (Tween™ 80) and sorbitan trioleate. The adjuvant may also be a combination of the TLR4 agonist MPL (3-O-desacyl-4'-monophosphoryl lipid A) and aluminum salt, e.g., AS04 (GlaxoSmithKline, Philadelphia, Pa.).

Certain adjuvants are commercially available as, for example, Merck Adjuvant 65 (Merck and Company, Rahway, N.J.); AS01, AS02, AS03, and ASO4 (GlaxoSmithKline, Philadelphia, Pa.); aluminum salts such as aluminum hydroxide gel (alum) or aluminum phosphate; biodegradable microspheres; monophosphoryl lipid A (MPL) and quil A.

In addition, the adjuvant composition can be one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a subject will support an immune response that includes Th1- and Th2-type responses. Optionally, the level of Th1-type cytokines will increase to a greater extent than the level of Th2-type cytokines. The levels of these cytokines may be readily assessed using standard assays. Certain adjuvants for eliciting a predominantly Th1-type response include, for example, a combination of monophosphoryl lipid A, preferably 3-de-O-acylated monophosphoryl lipid A, together with an aluminum salt adjuvants are available from Corixa Corporation (Seattle, Wash.). CpG-containing oligonucleotides (in which the CpG dinucleotide is unmethylated) also induce a predominantly Th1 response. Another adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins.

In some embodiments, the adjuvant is incorporated into the VLP in a membrane-anchored form. For example, GM-CSF or a bacterial flagellin protein containing a membrane anchor can be incorporated into the disclosed VLPs.

Pharmaceutical Compositions

The disclosed vaccines can be used therapeutically in combination with a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The materials may be in solution, suspension (for example, incorporated into microparticles, liposomes, or cells). Suitable carriers and their formulations are described in Remington: The Science and Practice of Pharmacy (22nd ed.) eds. Loyd V. Allen, Jr., et al., Pharmaceutical Press, 2012. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Pharmaceutical carriers are known to those skilled in the art. These most typically would be standard carriers for administration of vaccines to humans, including solutions such as sterile water, saline, and buffered solutions at physiological pH. Pharmaceutical compositions may include carriers, thickeners, diluents, buffers, preservatives, surface active agents and the like in addition to the vaccine. Pharmaceutical compositions may also include one or more active ingredients such as antimicrobial agents, antiinflammatory agents, anesthetics, and the like.

In some embodiments, the disclosed vaccines are formulated for delivery via intranasal, intramuscular, subcutaneous, transdermal or sublingual administration.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Combinations

The disclosed vaccine can be used to supplement existing human vaccines to improve cross protection. Therefore, the disclosed vaccine can further include (or be administered in combination with) a whole inactivated virus, split viral vaccine, live attenuated vaccine, or another virus-like particle (VLP) vaccine. For example, the disclosed vaccine can be combined with an inactivated vaccine, attenuated vaccine, split vaccine, or subunit vaccine. In some embodiments, the vaccine comprises the disclosed RSV F VLPs and at least one RSV split vaccine.

Methods of Vaccinating a Subject

A method of vaccinating a subject for RSV is disclosed that involves administering the disclosed vaccine to a subject in need thereof. The disclosed vaccine may be administered in a number of ways. For example, the disclosed vaccine can be administered intramuscularly, intranasally, or by microneedle in the skin. The compositions may be administered orally, intravenously, subcutaneously, transdermally (e.g., by microneedle), intraperitoneally, ophthalmically, vaginally, rectally, sublingually, or by inhalation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical dosage of the disclosed vaccine used alone might range from about 1 µg/kg to up to 100 mg/kg of body weight or more per vaccination, such as 10 µg/kg to 50 mg/kg, or 50 µg/kg to 10 mg/kg, depending on the factors mentioned above.

Symptoms of RSV are well known in the art. They include rhinorrhea, sore throat, headache, hoarseness, cough, sputum, fever, rales, wheezing, and dyspnea. Thus, the method of the invention comprises the prevention or reduction of at least one symptom associated with RSV infection. A reduction in a symptom may be determined subjectively or objectively, e.g., self-assessment by a subject, by a clinician's assessment or by conducting an appropriate assay or measurement (e.g. body temperature), including, e.g., a quality of life assessment, a slowed progression of a RSV infection or additional symptoms, a reduced severity of a RSV symptoms or a suitable assays (e.g. antibody titer and/or T-cell activation assay). The objective assessment comprises both animal and human assessments.

A number of embodiments of the invention have been described. Nevertheless, it will be understood that various modifications may be made without departing from the spirit and scope of the invention. Accordingly, other embodiments are within the scope of the following claims.

EXAMPLES

Example 1

RSV F VLP are shown to induce neutralizing antibodies and confers protection against RSV without pulmonary inflammation after challenge. RSV F VLP is similar to an enveloped virus in structure, 80-150 nm spherical particles in diameter but non-infectious. This F VLP avoids RSV vaccine-enhanced disease (VED) after RSV challenge, in contrasts with other RSV vaccines including FI-RSV (whole virus) (Connors, M., et al., 1992b. Journal of virology 66:7444-7451; Haynes, L. M., et al., 2003. J Virol 77:9831-9844), and F soluble proteins (Connors, M., et al., 1992a. Vaccine 10:475-484; Murphy, B. R., et al., 1990. Vaccine 8:497-502). Prior priming with RSV F VLP suppresses the induction of VED-prone lung inflammation that typically follows FI-RSV or F protein vaccination. RSV F VLP primes innate and adaptive immune responses suppressing VED, which differ from those primed by FI-RSV or purified F protein.

Avian cells that were transfected with plasmid DNA vectors encoding Newcastle disease virus (NDV) core proteins, M and NP, and containing two chimera proteins, composed of the RSV fusion protein (F) and glycoprotein (G) ectodomains fused to the NDV F and HN proteins were reported to produce chimeric RSV-NDV VLPs and their efficacy was tested in small animal studies (Cimica, V., et al., 2016. Clinical and vaccine immunology: CVI 23:451-459; Cullen, L. M., et al., 2015. J Transl Med 13:350). In these previous studies, chimeric RSV-NDV VLPs containing the pre-fusion RSV F protein were required at higher doses (50-150 µg) to stimulate protective immune responses in cotton rats (Cullen, L. M., et al., 2015. J Transl Med 13:350). RSV-NDV VLPs containing pre-fusion F with pre-F stabilizing mutations were shown to be effective in inducing RSV neutralizing antibodies but their immunogenicity was very low since high vaccine doses (50-150 µg) were needed for protective immune responses. Production of chimeric RSV-N DV VLPs in avian cells by DNA transfection would have limitations in scaling up the manufacturing process. The pre-fusion mutations (S155C, S290C, S190F, V207L 4 point mutations only) in the chimeric RSV-NDV VLP vaccine were different from those in our RSV F VLP vaccines containing the pre-fusion stabilizing mutations (mutations in the both furin cleavage sites, deletion of 10 amino acid residues, and 4 point mutations). Protective immunity was observed with moderate doses (10-20 µg) of RSV F VLP vaccines even with post-fusion F proteins. Recombinant baculovirus—insect cell expressed vaccine production would be easier and less vaccine cost than DNA transfection avian cell-expressed vaccine production. RSV neutralizing antibodies targeting to the pre-fusion F proteins were more potent than antibodies targeting to the post-fusion F proteins. Vaccines containing pre-fusion F conformation (and palivizumab reactive epitopes) were shown to be highly effective in inducing RSV neutralizing antibodies. Therefore, a pre-F (F12dm-dcm) VLP presenting pre-fusion F conformation, was created and shown to enhance RSV neutralizing immunogenicity.

Example 2

Antigenicity of different RSV vaccine platforms has not been well characterized, which is critically important for better understanding vaccine efficacy and safety (vaccine-enhanced disease after challenge).

The results of antigenicity tests (Table 1) suggest that RSV vaccines [RSV F VLP (F-WT VLP), FI-RSV, or split RSV] described above display high reactivity to palivizumab and 131-2a mAb but low or no reactivity to prefusion (pre-F) conformation F specific 5C4 mAb. Previous studies reported that immunization with post-fusion (post-F) protein presenting the neutralizing antigenic sites (I, II, IV) induces neutralizing antibodies clearing lung viral replication in mice and cotton rats after challenge.

However, post-F lacks an antigenic site 0 (504 mAb epitope, Table 1) which is uniquely present in pre-F. Recent studies demonstrate that RSV F vaccines containing pre-F and post-F conformation were more effective in inducing neutralizing antibodies. Vaccination of cotton rats with pre-F and post-F proteins primes VED despite lung viral clearance.

The efficacy and safety of VLP or virus (split RSV) presenting pre-F or both pre-F and post-F conformations are still not well known. We have developed unique RSV vaccine candidates presenting pre-F conformation dominantly in VLP and RSV vaccine platforms (Table 1). F-GCN4 TM (transmembrane) VLP is newly developed and contains the full-length F protein linked to oligomer-stabilizing domain (GCN4) and TM (transmembrane) from influeza virus hemmaglutinin proteins. F-GCN4 TM exhibits high post-F specific mAb [131-2a, palivizumab (Paliv.mab), Table 1].

Live RSV displays reactivity to both post-F (131-2a, Paliv.mab) and pre-F (5C4) specific mAbs as for a comparative control.

FI-RSV shows reactivity to 131-2a and palivizumab but not to 5C4, containing F in post-F conformation, consistent with a recent study {Killikelly, 2016 #108}.

Split RSV37° C. [standard preparation of inactivated split RSV vaccine] exhibits high reactivity to post-F (131-2a, Paliv.mab) and low reactivity to pre-F (5C4) specific mAbs.

Low temperature (4° C.) inactivation, split of RSV (split RSV4° C.) vaccines were shown to retain significantly higher levels of pre-fusion F conformation (Table 1). Split RSV4° C. (inactivated at 4° C. and split) showed high reactivity to pre-F specific 5C4 mAb than split RSV37° C. and FI-RSV (Table 1).

Subunit RSV post-fusion and pre-fusion F protein vaccines requiring adjuvants were able to induce RSV neutralizing antibodies but were found to induce vaccine-enhanced disease after challenge, raising vaccine safety concerns in animal models (Palomo, C., et al., 2016. J Virol 90:5485-5498; Schneider-Ohrum, K., et al., 2017. J Virol 91). Alum adjuvanted FI-RSV vaccination resulted in vaccine enhanced disease (VED) after RSV infection (Kapikian A Z, M. R., et al., 1969. American journal of epidemiology 89:405-421; Kim, H. W., et al., 1969. American journal of epidemiology 89:422-434).

Split RSV maintains sufficient immunogenicity to control lung viral titers in the absence of adjuvants, and induces a desirable T cell helper type 1 (Th1) response and avoids VED after RSV challenge,

TABLE 1

F VLP and RSV vaccine candidates with preF (5C4) or postF (131-21, palivizumab) specific mAb reactivity (Reactivity to F mAb by ELISA)

| F VLP or RSV | 131-2a | Palivizumab | 5C4 |
|---|---|---|---|
| F-WT TM (post F) | +++ | ++++ | +/− |
| F1m TM (post F) | ++++ | +++ | +/− |
| F + F1m TM (pre F) | + | + | ++++ |
| Fdcm TM (pre-F) | + | + | +++ |
| F12dm.dcm.VLP | ++ | ++++ | +++++ |
| Live RSV (A2 strain) | +++ | +++ | ++ |
| FI-RSV (post F) | ++++ | +++ | +/− |
| Split RSV37° C. | +++++ | +++++ | ++ |
| Split RSV4° C. | ++++ | ++++++ | ++++ |

VLP platforms were produced in insect cells. RSV vaccines were produced in HEp2 cells. ELISA OD values +/−: 0.1-0.2, +: 0.3-0.5, ++: 0.5-1, +++: 1-1.5, ++++: 1.5-2, +++++: 2-2.5, ++++++: >2.5

Example 3

RSV A2-L19F (expressing F protein of line 19F strain) was reported to retain higher levels of thermostable pre-F conformation than RSV A2 or DB1 strain in recent studies (Rostad, C. A., et al., 2017. J Virol. 92(6); Stobart, C. C., et al., 2016. Nat Commun 7:13916). Recombinant RSV A2-L19F strains were produced expressing dual F proteins in a pre-F-stabilized conformation using a bacterial artificial chromosome (BAC)-based reverse genetics technology.

Replication competent, recombinant RSV A2-L19F were generated with dual expression of F proteins where RSV NS2 virulence gene known as a virulence gene was replaced with F in the RSV A2-L19F to develop more effective and safe split RSV4° C. vaccine.

Transcript regulator M2-2 gene deletion was shown to increase the expression of F (Jin, H., et al., 2000. J Virol 74:74-82; Karron, R. A., et al., 2015. Sci Transl Med 7:312ra175; Teng, M. N., et al., 2000. Journal of virology 74:9317-9321). Generation of RSV A2-L19F expressing dual F proteins where M2-2 was replaced with F and tested in a split RSV 4° C. platform. F1m is a mutated-F protein that contains furin cleavage site 2 mutation (KKRKRR (SEQIDNO:7) to KKQKQQ(SEQIDNO:8)) in the F protein.

Heterologous F+F1m co-expression resulted in higher reactivity to 5C4 pre-F specific mAb (Table 1). A replicable recombinant RSV co-expressing F-WT and F1m TM was generated by replacing the M2-2 gene.

Example 4

The results of antigenicity tests (concentration at 0.05 μg/well, Table 1) suggest that RSV vaccines [F VLP (F-WT VLP), FI-RSV, or split RSV] described above display high reactivity to palivizumab (site II) and 131-2a (site I) mAb but low reactivity to prefusion (pre-F) F specific 5C4 monoclonal antibody (mAb). However, post-F lacks an antigenic site Ø (5C4 mAb epitope, Table 1) which is uniquely present in pre-F conformation. Alum-adjuvanted RSV F protein (post-F) vaccines were not sufficiently immunogenic for inducing protective levels of RSV neutralizing antibodies in the elderly (Falsey, A. R., et al., 2008. J Infect Dis 198:1317-1326; Langley, J. M., et al., 2009. Vaccine 27:5913-5919). RSV F vaccines containing pre-F (or both pre-F and post-F) were effective in inducing neutralizing antibodies (Cimica, V., et al., 2016. Clinical and vaccine immunology 23:451-459; Liang, B., et al., 2015. J Virol 89(18):9499-510; Palomo, C., et al., 2016. J Virol 90:5485-5498).

F1m TM VLP that contains furin cleavage site 2 mutation in the F protein displays similar antigenic properties as the F wild type context and did not show reactivity to 5C4 mAb. Heterologous F+F1m TM VLP was produced in insect cells by co-infecting with recombinant baculoviruses (rBVs) co-expressing F-WT and F1m TM. F+F1m TM VLP resulted in high reactivity to 5C4 pre-F specific mAb but low reactivity to palivizumab and 131-2a mAb, losing post-fusion epitopes (Table 1). Fdcm TM VLP (FIG. 5) contains known pre-fusion F conformation stabilizing mutations [DS-Cav1; S155C & S290C (DS), S190F & V207L (Cav1)] (McLellan, J. S., 2015. Curr Opin Virol 11:70-75; McLellan, J. S., et al., 2013. Science 342:592-598), expressed in a transmembrane (TM) anchor form on VLP. Fdcm TM VLP displays moderately high reactivity to 5C4 mAb but low reactivity to palivizumab and 131-2a mAb, losing post-fusion epitopes (Table 1).

Figure 2A:
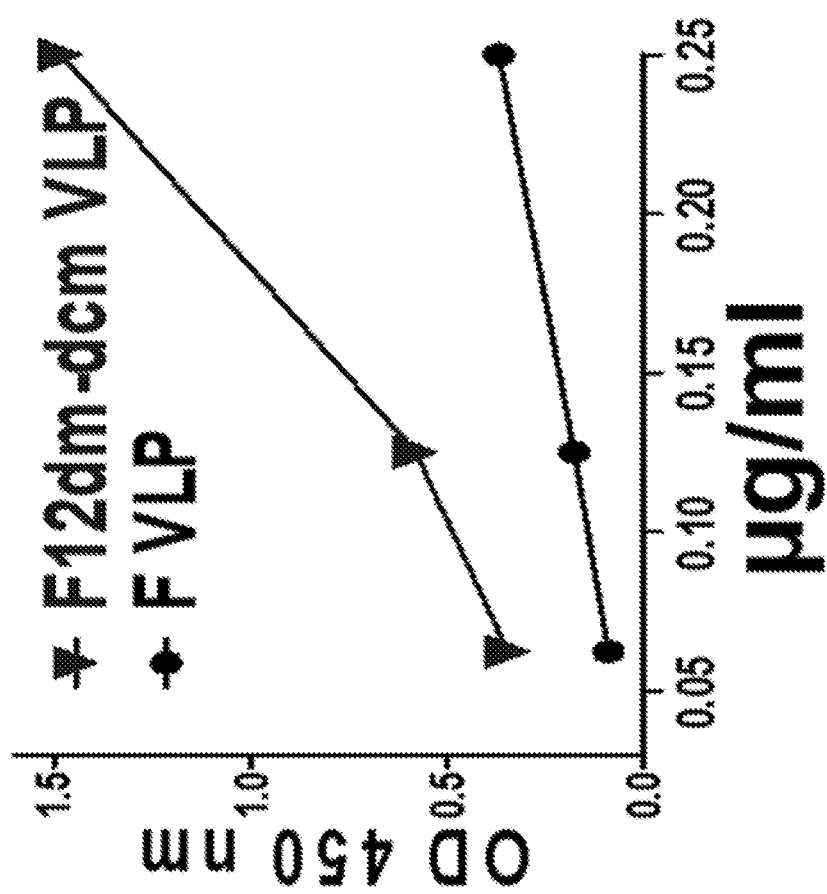
FIG. 2A is a graph showing reactivity of F12dm-dcm VLP to 5C4 mAb.

Both mutations were combined to develop a unique F construct, named F12dm-dcm VLP presenting very high reactivity to both 5C4 mAb (pre-F) and palivizumab (Table 1, FIG. 2A). This pre-F (F12dm-dcm) construct contains both mutations in the furin cleavage sites 1 and 2, deletion of 10 amino acids in the fusion peptide region, as well as pre-fusion F conformation stabilizing mutations [DS-Cav1; S155C & S290C (DS), S190F & V207L (Cav1)] (McLellan, J. S., 2015. Curr Opin Virol 11:70-75; McLellan, J. S., et al., 2013. Science 342:592-598), and was expressed with a transmembrane (TM) form on VLP (FIG. 2A).

Figure 2B:
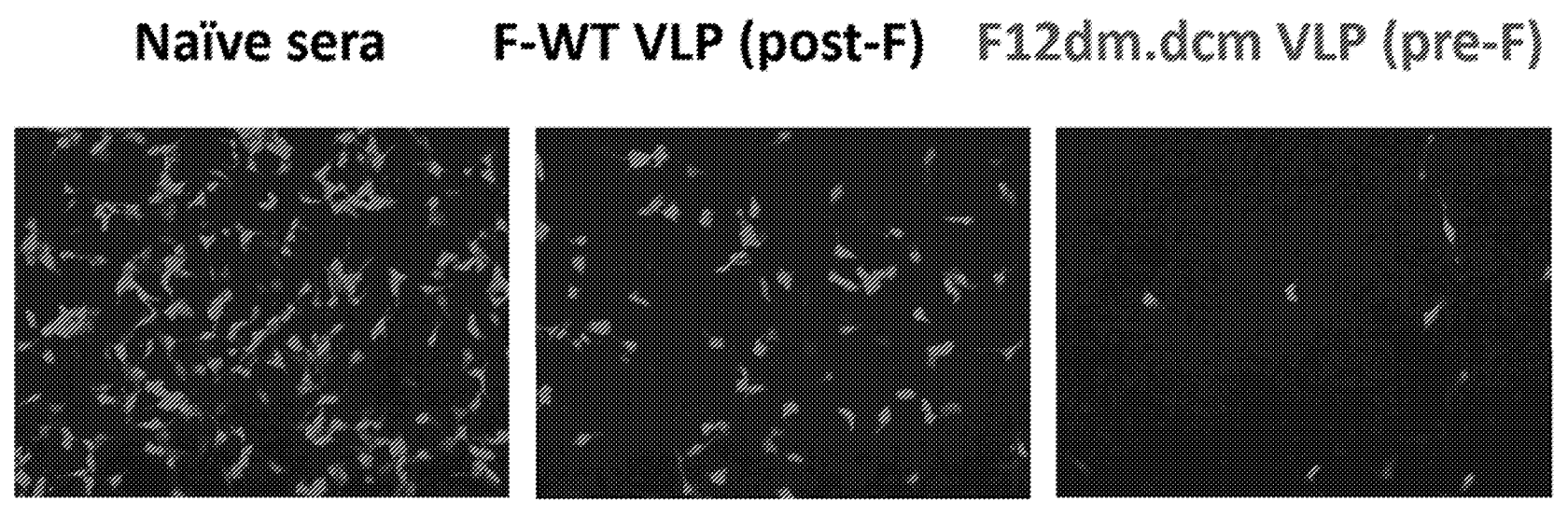

Data using mouse sera after IM prime boost immunization with pre-F (F12dm.dcm) VLP showed higher and potent RSV neutralizing activity than F-WT VLP immune sera (FIG. 2B) using red fluorescent RSV A2-K-L19F on Vero cells. Therefore, pre-F (F12dm.dcm) VLP containing pre-F conformation (Table 1) is highly effective in inducing RSV neutralizing antibodies, thereby enhancing protective immunity while priming away from VED.

Example 5

Figure 3B:
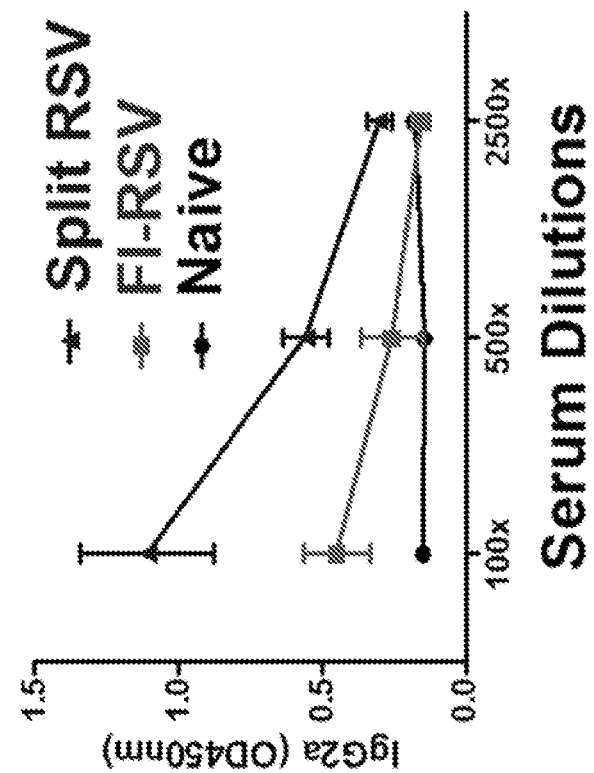
FIG. 3B shows RSV F specific IgG2a antibodies after prime immunization of adult BALB/c mice.
Figure 3A:
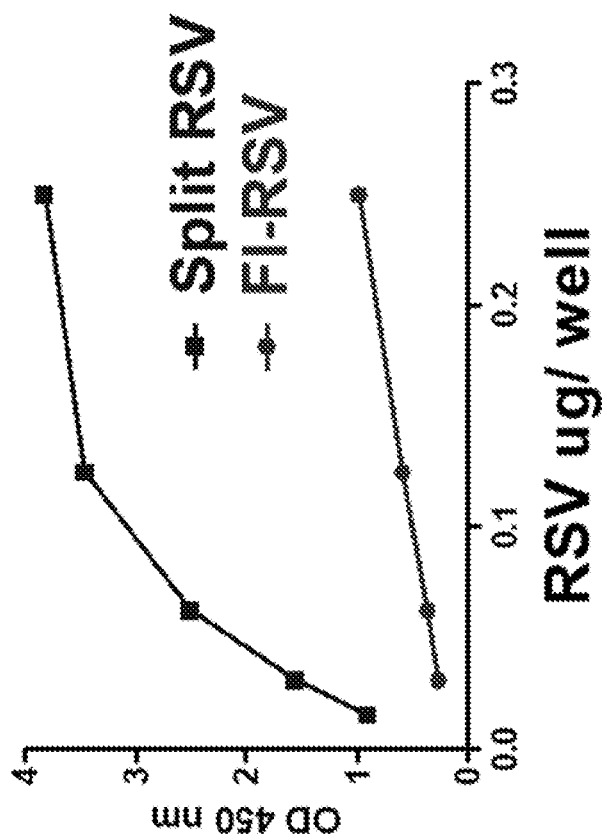
FIG. 3A shows reactivity (ELISA) of FI-RSV and Split RSV to Palivizumab.

FI-RSV shows reactivity to 131-2a and palivizumab but not to 5C4 mAb (Table 1), suggesting post-F, consistent with a previous study (Killikelly, A. M., et al., 2016. Sci Rep 6:34108). Split RSV37° C. (inactivated at 37° C. and split, a standard preparation) exhibits high reactivity to post-F (131-2a, Paliv.mab) and a moderate reactivity to pre-F (5C4) specific mAbs (FIG. 3A). Split RSV4° C. (inactivated at low temperature (4° C.) and split) showed high reactivity to pre-F specific 5C4 mAb than split RSV37° C. and FI-RSV (Table 1). RSV A2-L19F (expressing F protein of line 19F (L19F) strain) was reported to retain higher levels of thermostable pre-F conformation than RSV A2 or DB1 strains (Rostad, C. A., et al., 2017. J Virol. 92(6); Stobart, C. C., et al., 2016. Nat Commun 7:13916). Therefore, split RSV4° C. A2-L19F is highly effective in inducing RSV neutralizing antibodies, thereby enhancing protective immunity while priming away from VED.

Example 6

Figure 3C:
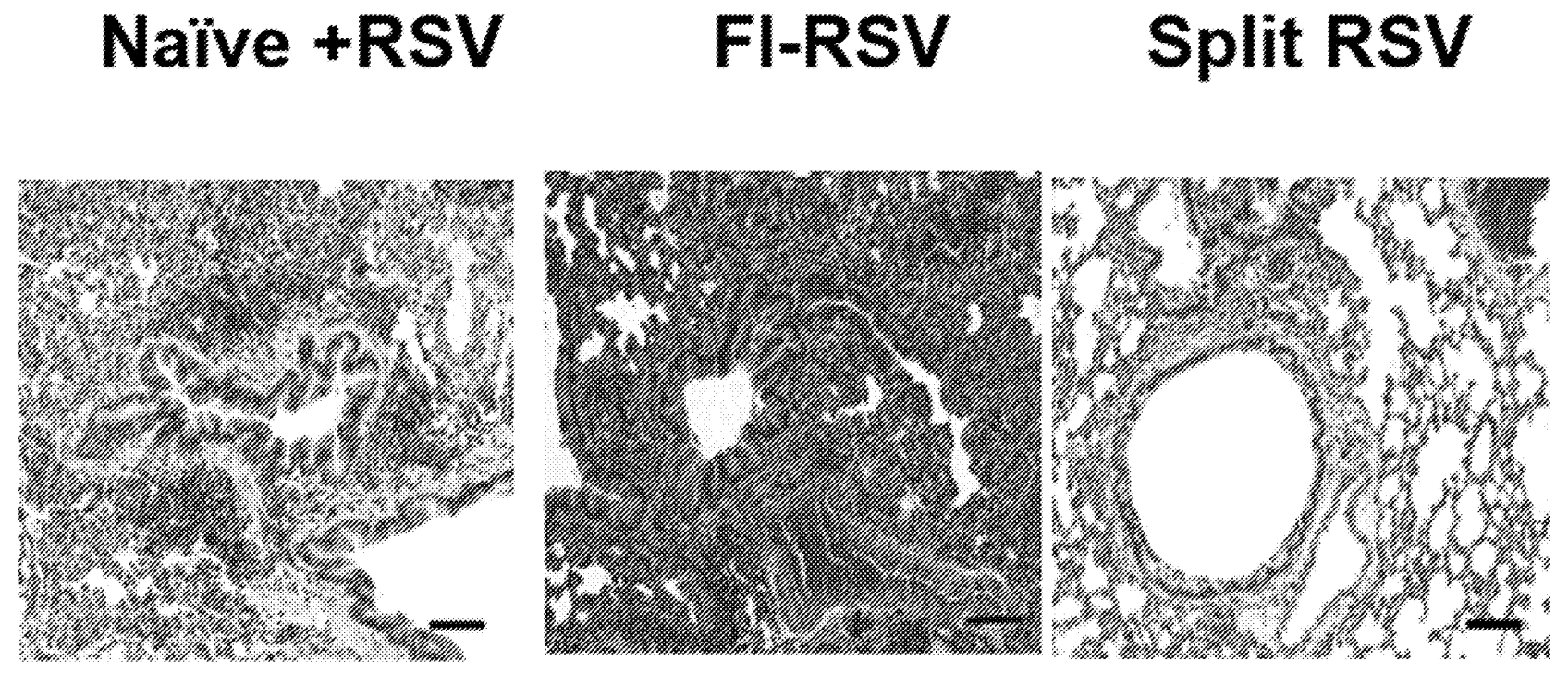

To compare immunogenicity, BALB/c mice (n=10) were IM primed (a single dose) with 5 μg of split RSV or FI-RSV. Split RSV raised higher levels of IgG2a than FI-RSV (FIG. 3B) and controlled lung viral titers even after prime (unpublished data). Importantly, split RSV vaccination induced no or low levels of pulmonary histopathology compared to naïve mice+RSV or the FI-RSV group displaying severe lung inflammation after RSV challenge ($1\times10^6$ PFU) (FIG. 3C).

These results demonstrate desirable properties of split RSV as a promising vaccine candidate: [1] higher reactivity to palivizumab, [2] effective protection with Th1-like immune responses, [3] less likely to induce VED, and [4] more immunogenic and protective even without adjuvants (FIG. 5). In contrast, soluble F protein RSV vaccines were low immunogenic and required adjuvants to induce RSV neutralizing antibodies (Murphy, B. R., et al., 1990. Vaccine 8:497-502; Schneider-Ohrum, K., et al., 2017. J Virol 91).

Example 7

Alum adjuvant increases FI-RSV vaccine efficacy (lowering lung viral loads) but promotes vaccine-enhanced disease VED (Kim, K. H., et al., 2015. PloS one 10:e0139916). Squalene oil-in-water emulsion (Lambert, S. L., et al., 2015. PloS one 10:e0119509; Schneider-Ohrum, K., et al., 2017. J Virol 91), delta-inulin (Wong, T. M., et al., 2016. Human vaccines & immunotherapeutics:1-10), and natural killer (NK) T cell agonist α-GalCer (Johnson, T. R., et al., 2002. J Virol 76:4294-4303) did not diminish lung inflammation of RSV vaccines. CpG is an oligodeoxynucleotide with unmethylated CpG motifs and recognized by TLR9 on human B cells and dendritic cells, inducing Th1-dominant immune responses (Krug, A., et al., 2001. Eur. J. Immunol. 31:3026-3037; Lin, L., et al., 2004. Eur J Immunol 34:1483-1487; McCluskie, M. J., et al., 1998. J. Immunol. 161:4463-4466; Vicari, A. P., et al., 2007. Antivir Ther 12:741-751). RSV F protein vaccines with high dose of CpG (20-100 μg) adjuvant did not prevent lung pathology after challenge of vaccinated cotton rats (Prince, G. A., et al., 2003. J Virol 77:13156-13160). Other studies reported high dose CpG (10-100 μg) adjuvant effects on improving the efficacy but lacked the details on VED in the RSV F protein vaccines (Garlapati, S., et al., 2012. Vaccine 30:5206-5214; Hancock, G. E., et al., 2001. Vaccine 19:4874-4882; Oumouna, M., et al., 2005. Journal of virology 79:2024-2032). MPL (3-O-deacyl-4'-monophosphoryl lipid A), an attenuated version of TLR4 agonist lipopolysaccharide (LPS), is included in human vaccines (Rappuoli, R., et al., 2011. Nature reviews. Immunology 11:865-872). ASO4™ (GSK) of combined alum+MPL adjuvant is approved for use in human vaccines (HPV, HBV) (Boland, G., et al., 2004. Vaccine 23:316-320; Giannini, S. L., et al., 2006. Vaccine 24:5937-5949; Harper, D. M., 2009. Expert review of vaccines 8:1663-1679; Khatun, S., et al., 2012. Japanese journal of clinical oncology 42:36-4; Levie, K., et al., 2002. Scandinavian journal of infectious diseases 34:610-614; Thoelen, S., et al., 1998. Vaccine 16:708-714). A high dose MPL (100 μg) was shown to attenuate FI-RSV-induced histopathology and proinflammatory cytokines (Boukhvalova, M. S., et al., 2006. Vaccine 24:5027-5035; Prince, G. A., et al., 2001. J Gen Virol 82:2881-2888).

Many adjuvants were screened (Tables 2 and 3). A unique combination of low dose [MPL TLR4 agonist+CpG TLR9 agonist] adjuvant was shown to enhance vaccine efficacy and prevent RSV vaccine-enhanced lung histopathology (FIGS. 5A-5B) at 5- to 50-fold lower dose ranges than those reported in previous studies. BALB/c mice (6 weeks old adults, n=5) were IM prime boost vaccinated with purified RSV F protein (0.3 μg)±alum (50 μg) or combined CpG (1 μg)+MPL (4 μg) adjuvant. Mice were challenged with RSV A2 ($1\times10^6$ PFU) at 6 weeks after boost and sacrificed to determine RSV vaccine-enhanced lung inflammation (FIGS.

Figure 4:
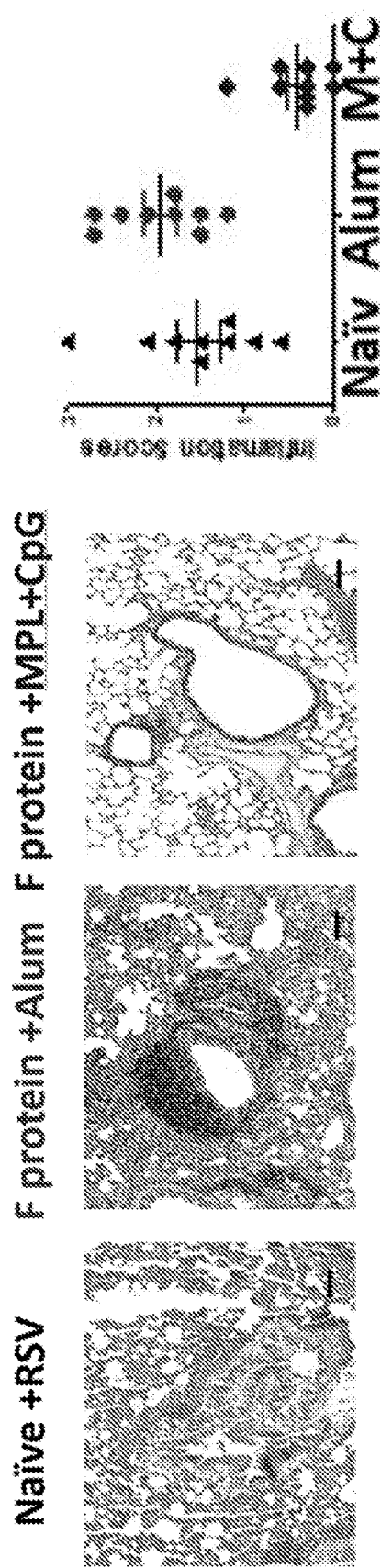
FIG. 4 shows CpG+MPL adjuvanted RSV F protein vaccination suppresses lung histopathology (VED) after RSV challenge (1×10$^6$ PFU). Naïve+RSV: Naïve infection, F protein+Alum: F protein (0.3 µg)+alum adjuvant (25 µg), F protein+M+C: F protein (0.3 µg)+CpG (4 µg)+MPL (1 µg).

4-5). The F protein only and alum groups showed severe histopathology whereas the CpG+MPL group displayed no lung histopathology. A combination of low dose CpG+MPL (4 μg+1 μg) prevents vaccine-associated lung histopathology due to RSV F protein vaccination (FIG. 4) and further improves the efficacy of split RSV vaccination by further preventing VED (FIG. 5).

Example 8

Low dose [MPL TLR4 agonist+CpG TLR9 agonist] adjuvant improved the cross protective efficacy of influenza split virus vaccine (Tables 2-3). To compare adjuvant efficacy in 14 days old (D14) infant mice, split influenza (flu) virus vaccine (0.5 μg)+/−adjuvants was used with low doses of adjuvants: MPL (0.5-1 μg), CpG (2-4 μg) vs 10-100 μg in prior studies (Mosca et al., 2008; Opal et al., 2005). After intramuscular (i.m.) priming (single exposure) of D14 mice with split flu (0.5 μg)+/−adjuvants (alum 25 μg, MPL 1 μg, CpG 4 μg, MPL 1 μg+Alum 25 μg, MPL 1 μg+CpG 4 μg), serum IgG isotype Abs, and protection against intranasal (i.n.) lethal challenge with homologous virus (pandemic A/California/2009, pH1N1) at 4 W later (Table 2) was determined. Combined low dose MPL (1 μg)+CpG (4 μg) TLR agonist adjuvant was found to be effective in inducing IgG2a (T helper type 1) isotype antibodies in D14 mice. Also, MPL+CpG significantly improved protection against lethal infection with body weight (BW) loss 2%, similar to AddaVax (an equivalent MF59 licensed adjuvant) in D14 pups (BW loss 1-2%) compared to D14 split alone (BW loss 14.4%) and other adjuvants (BW loss 7-11.7%, Table 2).

TABLE 2

Superior efficacy of MPL + CpG adjuvants on enhancing influenza vaccine efficacy in infant age mouse models

| Age Groups | IgG1 | IgG2a | BW (%) |
|---|---|---|---|
| Naïve inf. (lethal) | 0.08 | 0.04 | >25% |
| adult split (0.5 μg) | 0.60 | 0.21 | 13.0% |
| D 14 split | 0.63 | 0.06 | 14.4% |
| D 14 split + alum | 0.92 | 0.08 | 11.7% |
| D 14 split + MPL + Alum | 0.87 | 0.12 | 8.9% |
| D 14 split + MPL (1 μg) | 0.89 | 0.30 | 7.0% |
| D 14 split + CpG (4 μg) | 0.51 | 0.19 | 9.4% |
| D 14 split + MPL + CpG | 0.41 | 0.54 | 2.0% |
| Naïve inf. | 0.08 | 0.04 | 21% |
| D 7 split | 0.44 | 0.04 | 18% |
| D 7 split + MPL + CpG | 0.95 | 0.15 | 6% |
| D 7 split + AddaVax | 0.17 | 0.05 | 25% |
| D 7 split + polyI:C | 0.13 | 0.04 | 24% |
| D 5 split | 0.08 | 0.03 | >25% |
| D 5split + MPL + CpG | 0.54 | 0.12 | 11% |

Split: Inactivated influenza split vaccine
Adjuvants: alum, AddaVax, MPL, CpG, MPL + CpG, poly I:C
DK128 (killed lactic acid bacteria), CWS (Cell-wall cytoskeleton of BCG vaccine: Bacillus Calmette-Guérin (BCG))

TABLE 3

Effects of new adjuvants on enhancing the protective efficacy of influenza vaccines efficacy in infant and adult age mouse models

| Age Groups | IgG1 | IgG2a | BW (%) |
|---|---|---|---|
| B6 Naïve inf. (lethal) | 0.08 | 0.04 | >25% |
| B6 adult split (3 μg) | 0.60 | 0.15 | >25% |
| B6 adult split (3 μg) + DK128 | 2.60 | 2.2 | 10% |

TABLE 3-continued

Effects of new adjuvants on enhancing the protective efficacy of influenza vaccines efficacy in infant and adult age mouse models

| Age Groups | IgG1 | IgG2a | BW (%) |
|---|---|---|---|
| D 6, D 14 prime boost vaccination | | | |
| D 6 Naïve Inf. | 0.08 | 0.04 | >25% |
| D 6 Split only | 0.7 | 0.12 | 22% |
| D 6 Split + CWS | 1.4 | 0.2 | 6% |
| D 14 Naïve Inf. | | | 20% |
| D 14 Split only | 0.75 | 0.05 | 20% |
| D 14 Split + CWS | 1.3 | 0.64 | 9% |

Example 9

Adjuvant effects of low dose MPL+CpG adjuvant were determine in neonatal age mice [5 days old: D5; 7 days old: D7] in comparison with other adjuvants. Severe BW loss (%) was observed in neonatal pups primed intraperitoneally (i.p.) with split flu alone (D5 split 0.1-0.5 μg, >25% BW loss) or plus AddaVax (D7split+AddaVax [(an equivalent MF59 licensed adjuvant], BW loss 25%), poly IC (4 μg) [polyinosinic-polycytidylic acid, TLR3 agonist] (D7split+ poly IC, 24%). MPL+CpG TLR adjuvant was superior to other adjuvants in inducing IgG antibodies and protection in D5/D7 age neonatal mice (BW 6-11%, FIG. 4). It is a novel discovery that MPL+CpG adjuvant in split flu (0.1 μg) prime induces improved protection in neonatal (D5/7) age mice (Table 2).

Example 10

The adjuvant effects on influenza vaccine efficacy of heat-killed lactic acid bacteria (DK128) and cell wall skeleton (CWS) of Bacillus Calmette-Guérin (BCG) were tested in mice. Both heat-killed DK128 and BCG CWS showed vaccine adjuvant effects on enhancing the immunogenicity and efficacy of inactivated split influenza virus vaccines even in the immune compromised condition (Table 3).

Example 11

Figure 6A:
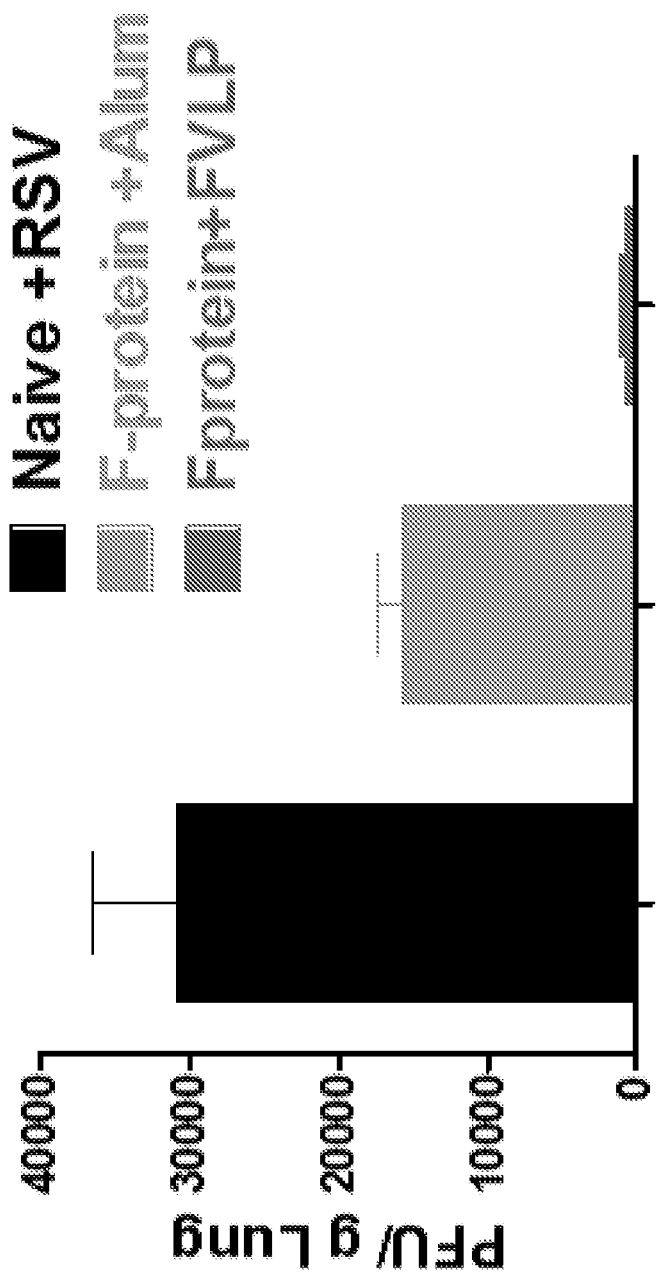
FIG. 6A shows RSV lung viral titers after F VLP co-vaccination.
Figure 6B:
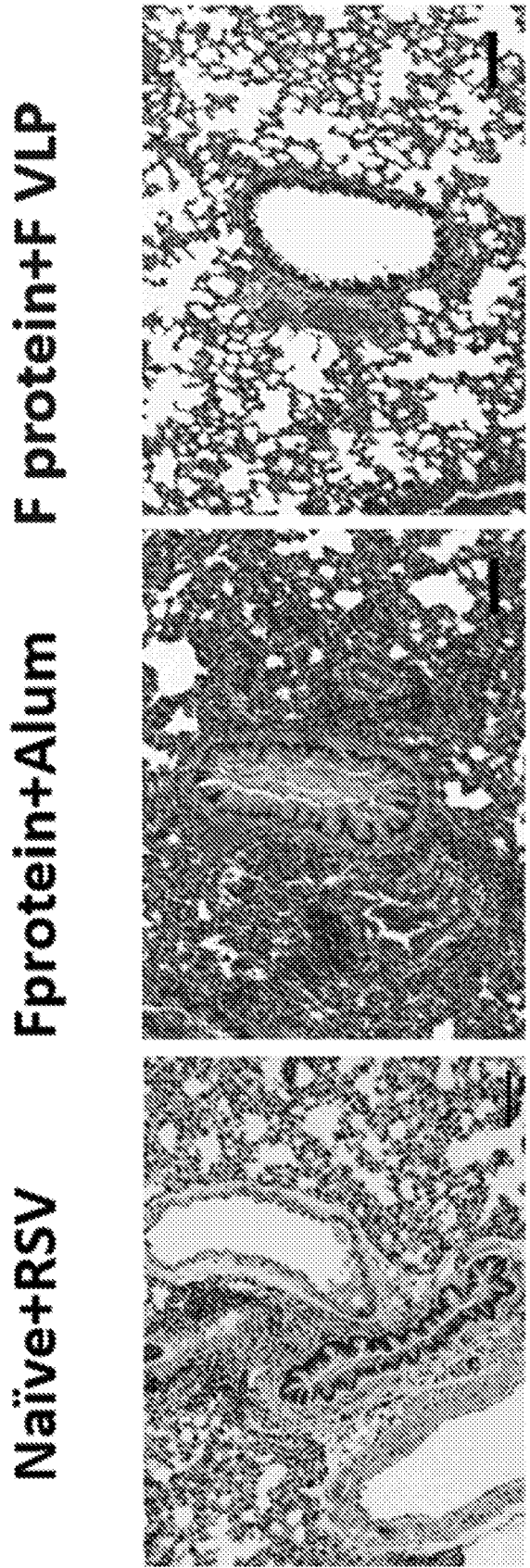
FIG. 6B shows lung histopathology after RSV challenge (1×10$^6$ PFU RSV A2). Infant (2W old) mice (n=6) were IM primed with F protein (0.3 µg)+alum (30 µg) or F protein (0.3 µg)+F VLP (with 0.3 µg F), and then challenged 3 weeks later. (Bars: 100 µm).

F VLP was found to prime immune responses preventing VED upon exposure to FI-RSV. BALB/c mice (n=5) were intramuscularly (IM) immunized with FI-RSV (prime)/FI-RSV (boost) or heterologous F VLP prime/FI-RSV boost. RSV F VLP prime was found to dictate the pattern of RSV-specific IgG2a (Th1 type) IgG responses (IgG2a/IgG1 ratios=4) after heterologous F VLP prime/FI-RSV boost; whereas FI-RSV prime-boost induced IgG1 predominantly (IgG2a/IgG1 ratios <1). FI-RSV/FI-RSV and F VLP/FI-RSV vaccination controlled lung RSV titers after RSV challenge. RSV F VLP prime was found to suppress lung inflammation by subsequent FI-RSV boost. To further extend this exciting finding, VED-prone purified RSV F protein vaccines were tested in infant mice that are prone to RSV disease. IM prime co-immunization of 2 weeks (2 W) old infant BALB/c mice with F VLP+F protein induced higher levels of RSV specific IgG2a (Th1 type) antibodies, and resulted in better control of lung viral titers (immune plaque assay) after RSV challenge compared to alum adjuvanted-F protein (FIG. 6A). Importantly, co-vaccination of RSV F VLP+F protein avoided VED of F protein-enhanced lung pathology after RSV challenge (FIG. 6B). Alum adjuvanted-F protein primed-mice induced lung inflammation and periodic acid-Schiff stain (PAS+) mucus production in the airways after RSV challenge (FIG. 3B) consistent with other studies (Murphy, B. R., et al., 1990. Vaccine 8:497-502; Schneider-Ohrum, K., et al., 2017. J Virol 91).

Example 12

Figure 7A:
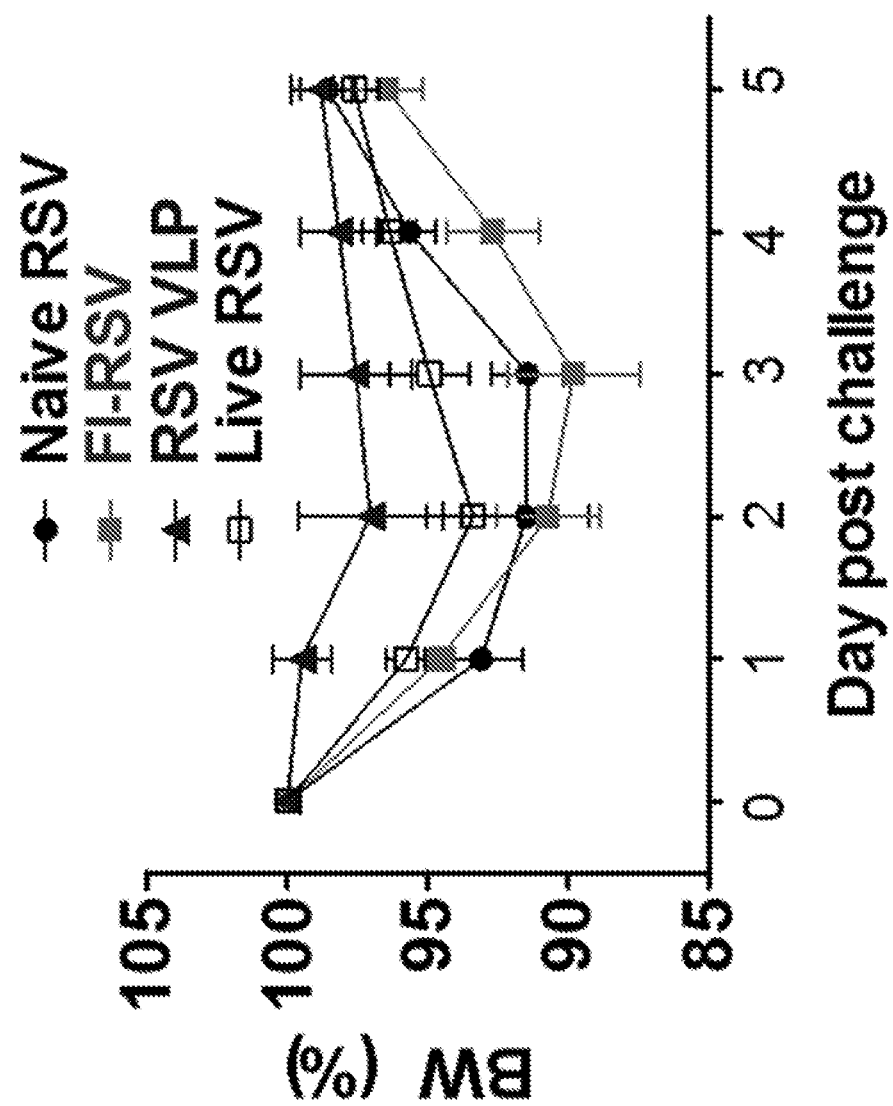
Figures 7B, 7C:
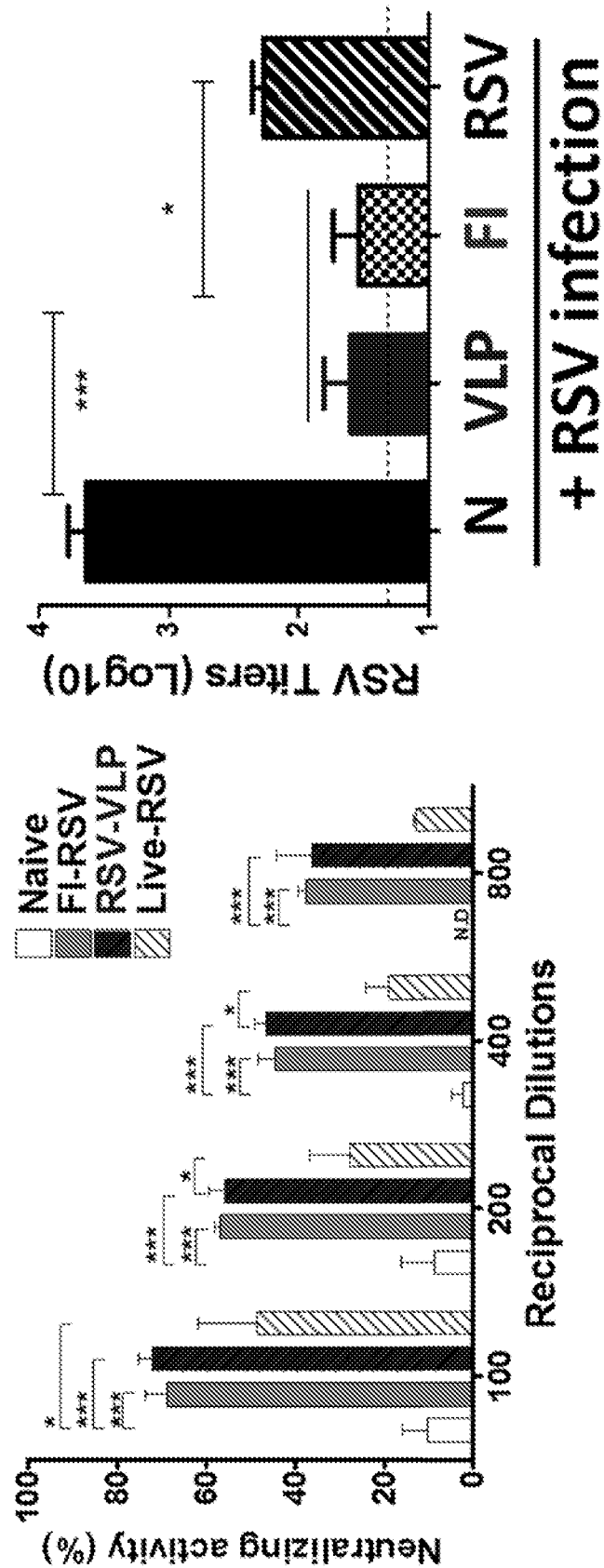
Figure 7D:
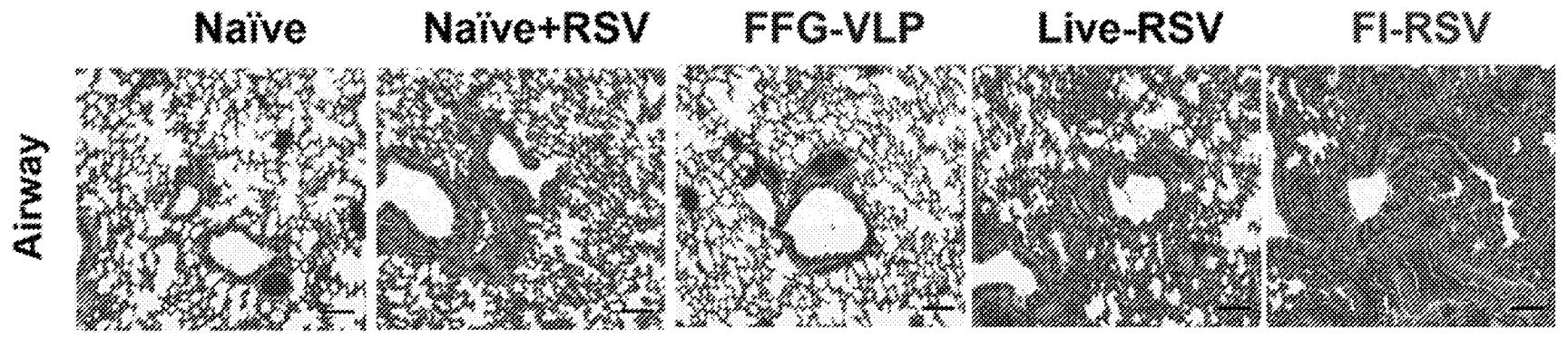

Groups of BALB/c mice were prime or prime-boost intramuscularly (IM) immunized with RSV (FFG) VLP (F DNA 25 µg+F VLP 10 µg), FI-RSV (2 µg), or inoculated with live RSV (1×10⁴ PFU), and then challenged with RSV (1×10⁶ PFU RSV A2) (FIG. 7). RSV VLP confers protection against RSV by clearing lung viral loads (FIG. 7B), yet avoids VED [FIG. 7A, weight loss, 7C. lung histopathology of hematoxylin and eosin (H&E)]. Whereas FI-RSV or prior exposure to live RSV cause severe to moderate levels of weight loss and histopathology (FIG. 7).

Figure 8A:
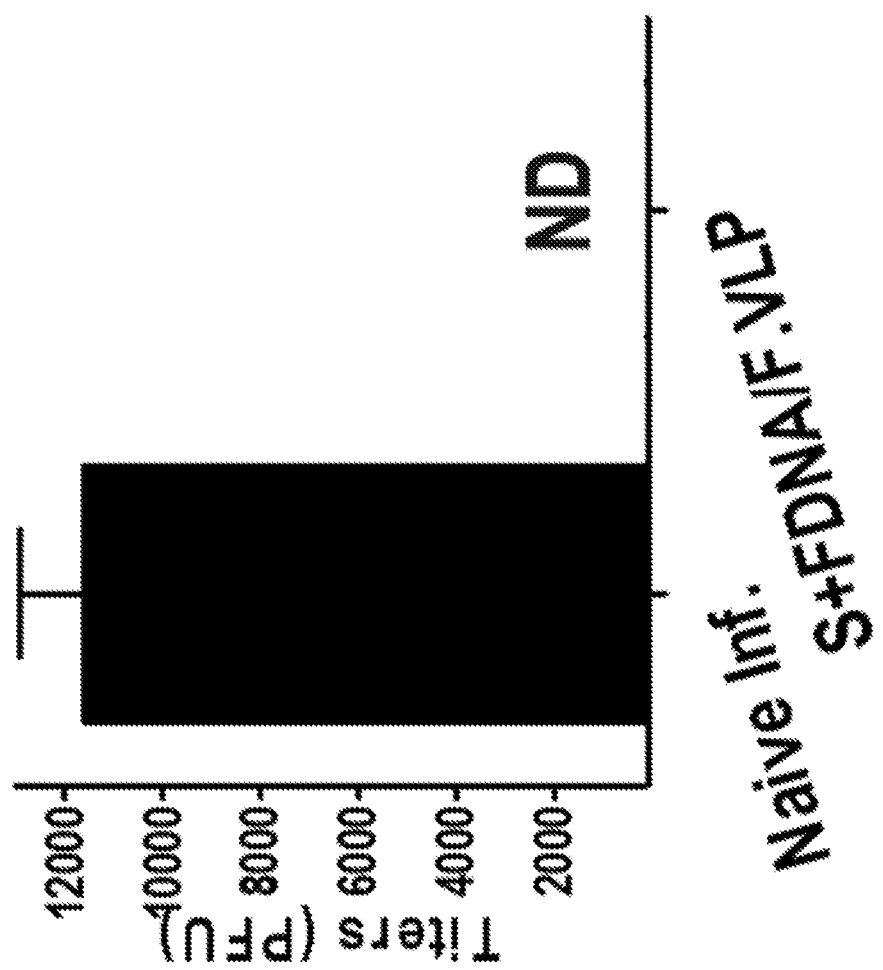
FIGS. 8A and 8B show neonatal cotton rats (n=5) primed with Split RSV (10 μg)+F DNA (10 μg)/boost F VLP (10 μg) were protected against RSV without histopathology.
Figure 8B:
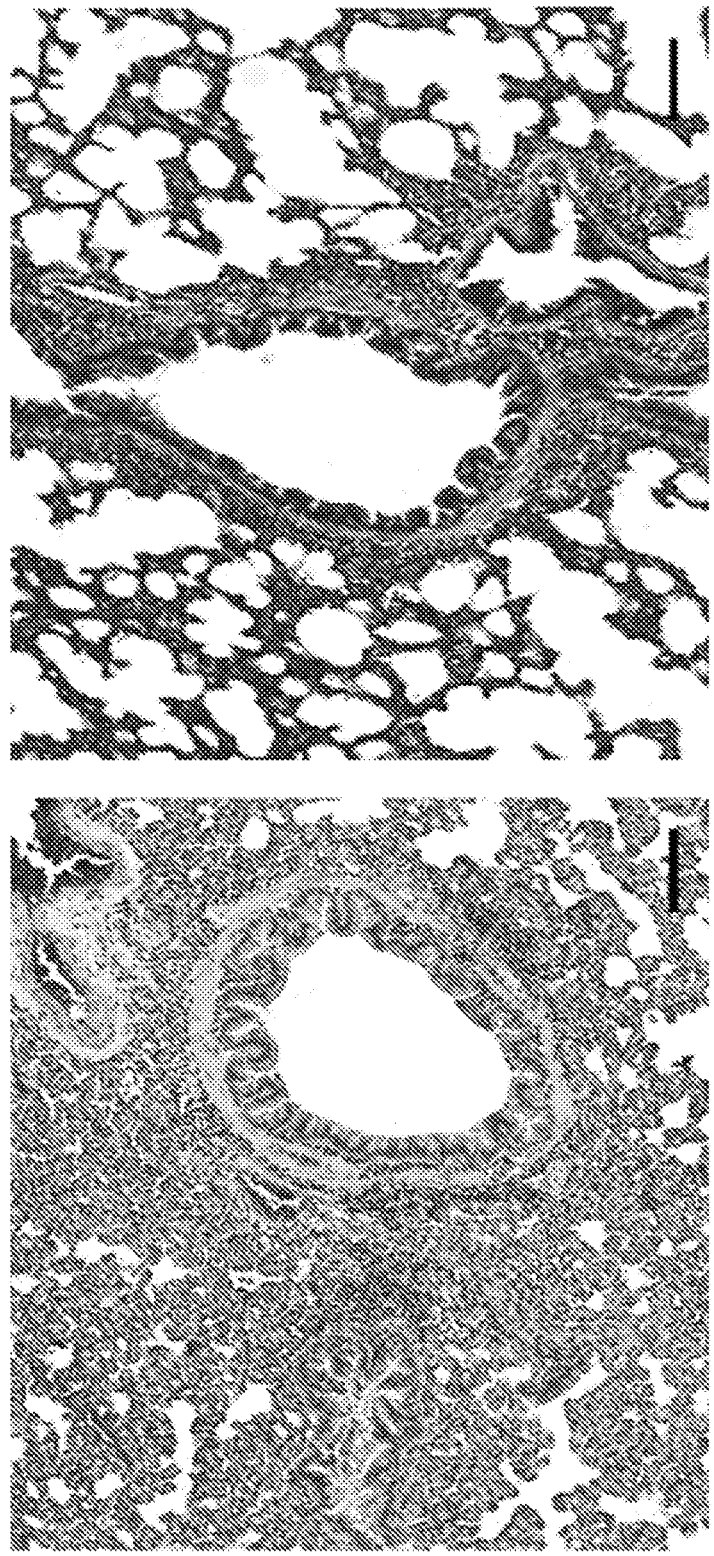
Figure 9A:
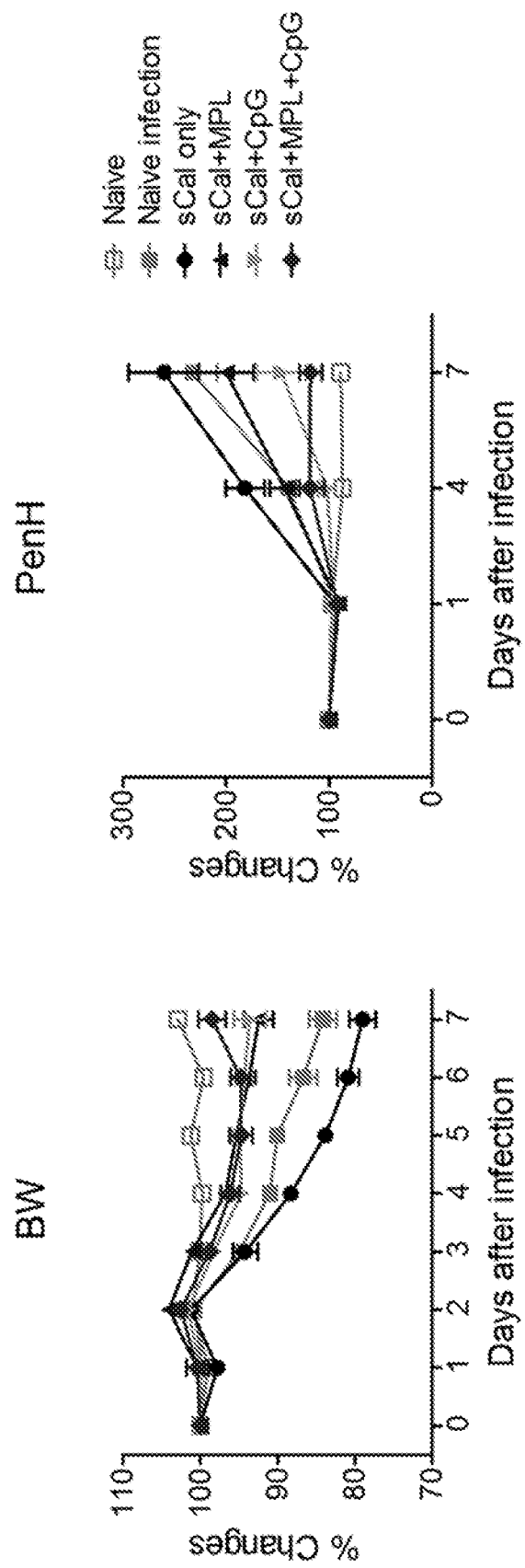
Figure 10A:
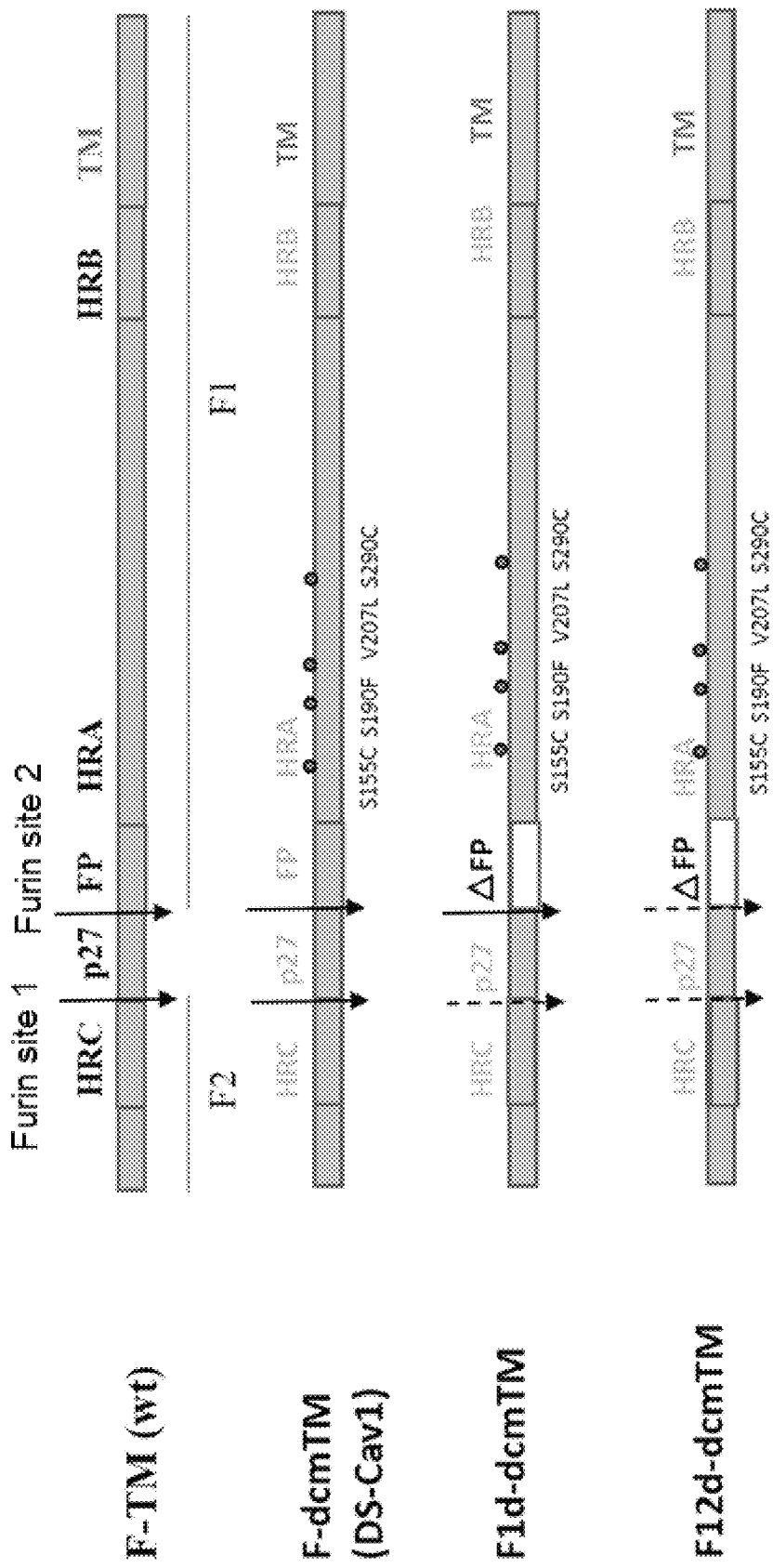
FIGS. 10A and 10B are diagram of mutant F gene constructs to be presented on VLPs.
Figure 10B:
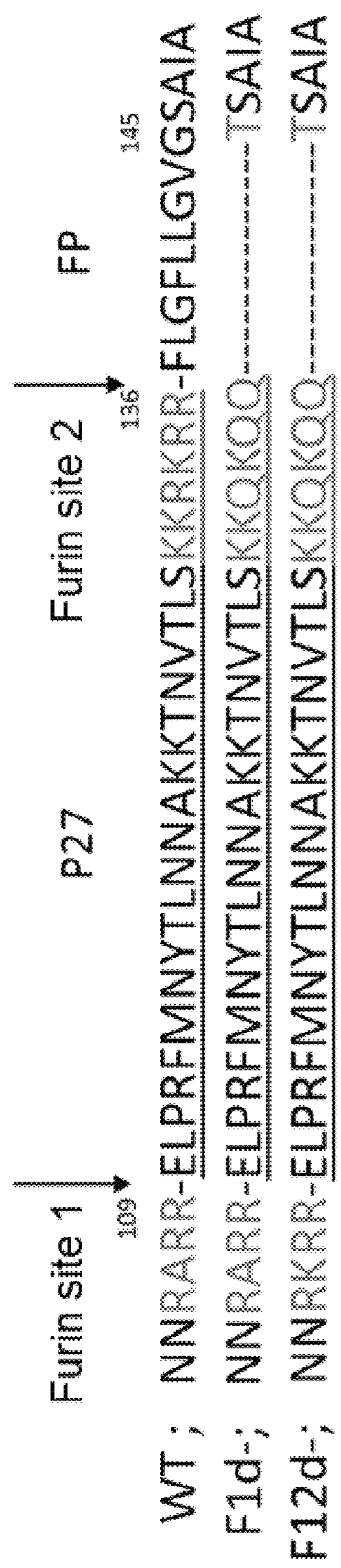
Figure 11B:
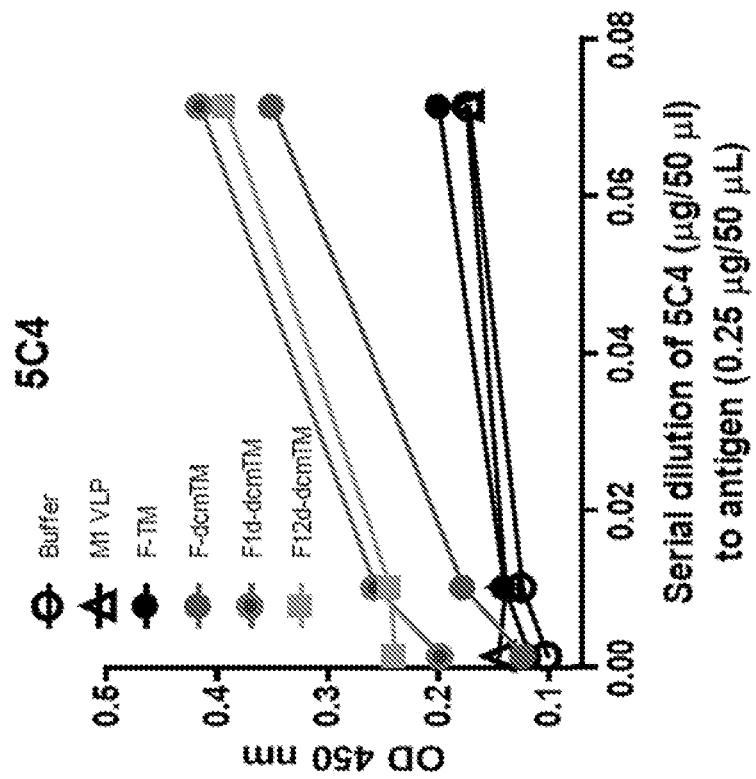
FIGS. 11A to 11E show antigenic profiles of mutant RSV F proteins in TM VLPs. WT (F-TM), and mutant F protein (F-dcmTM, F1d-dcmTM, F12d-dcmTM) VLPs were coated in serial dilution on 96-well plates.
Figure 11A:
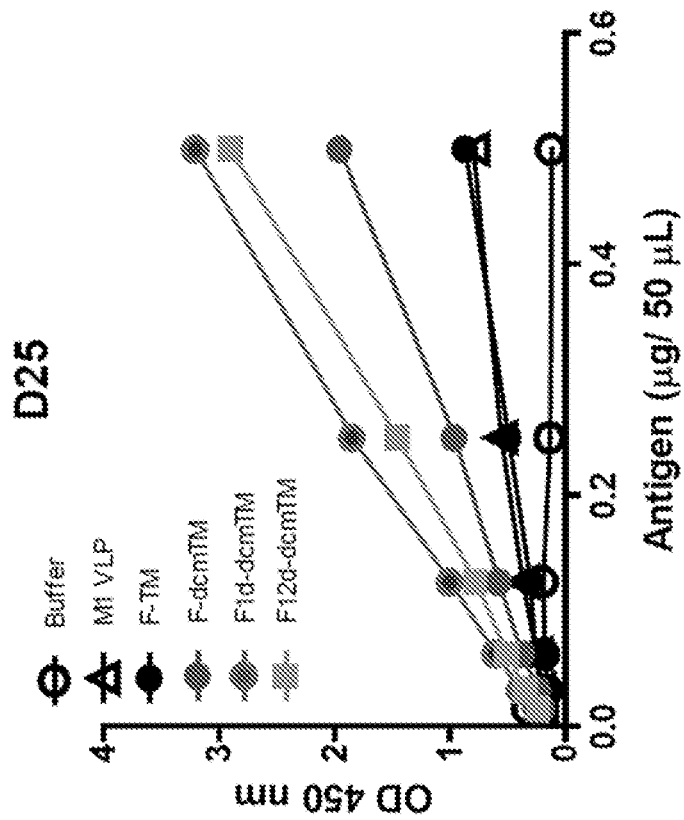
Figures 11C, 11D:
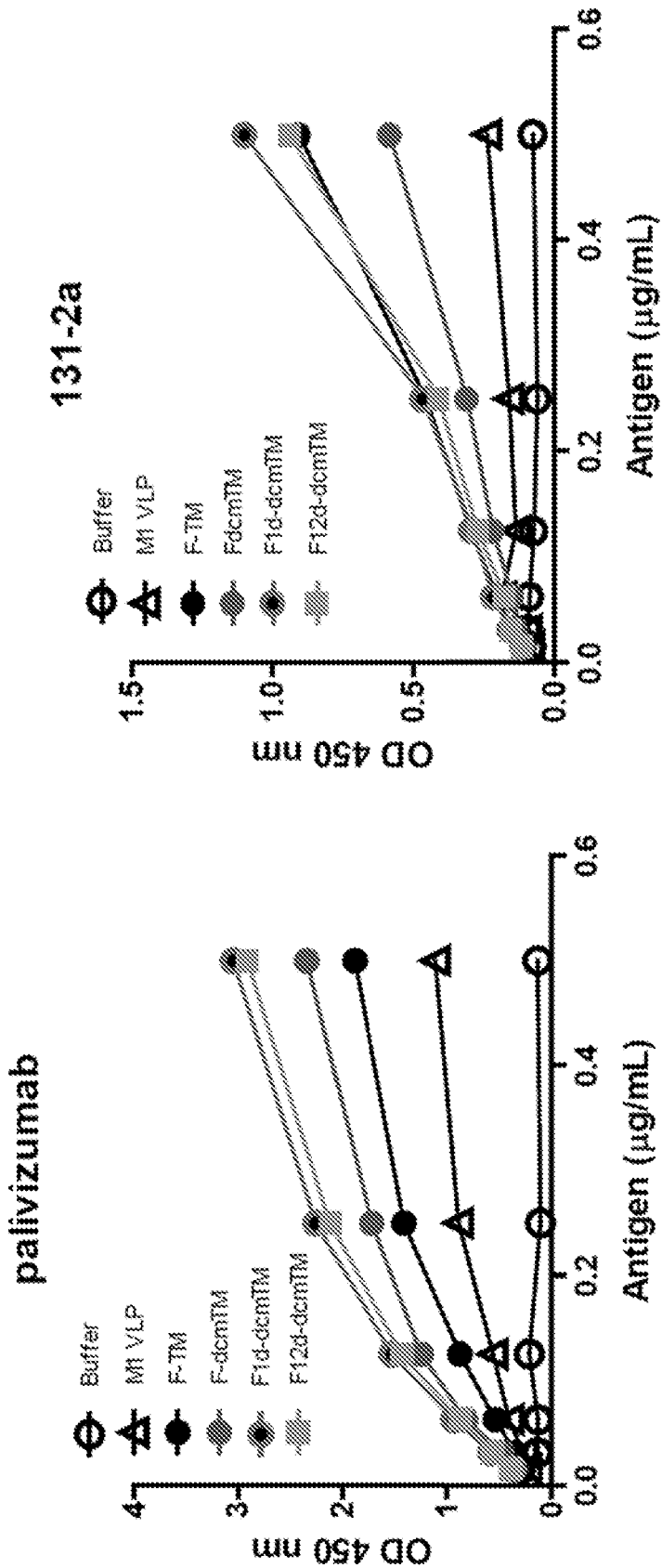
Figure 11E:
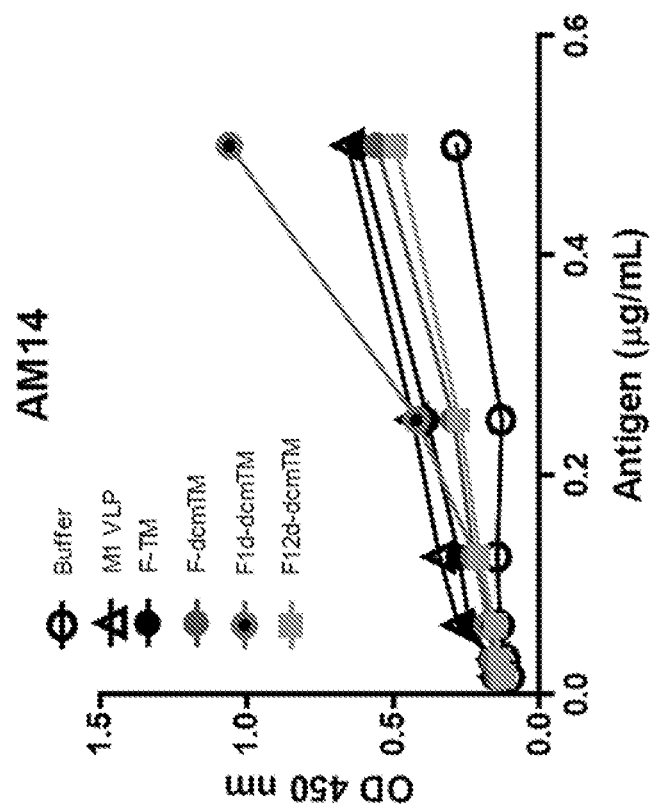
Figure 12:
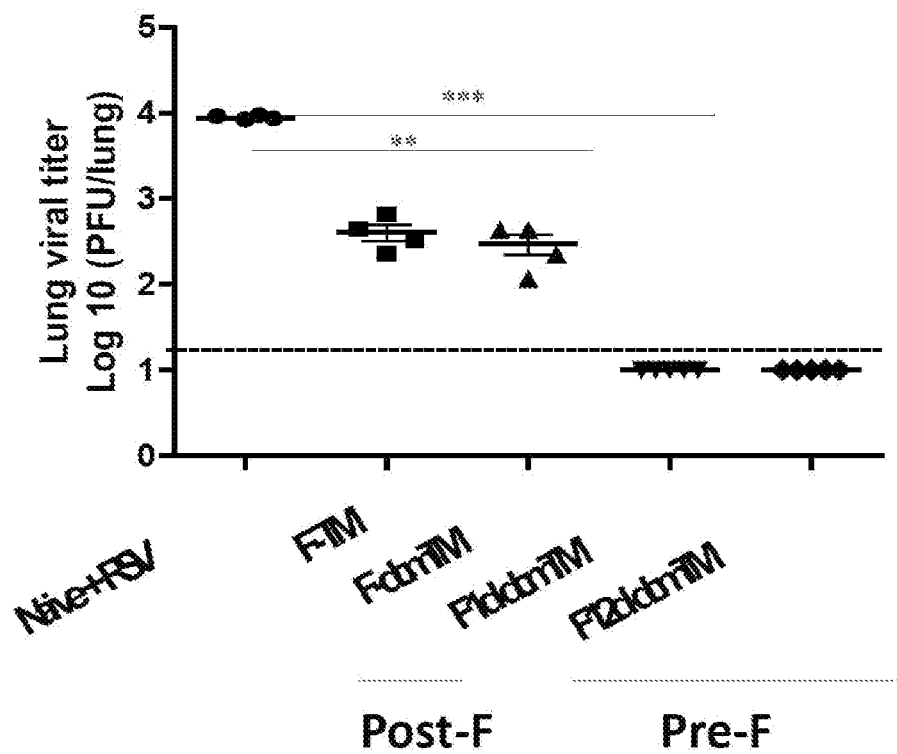
FIG. 12 shows F1d-dcmTM and F12d-dcmTM VLP immunized mice clear lung viral loads after RSV challenge. Lungs from individual mice in the groups (n=5) were collected on day 5 post challenge ($5×10^5$ PFU/mouse i.n.) in each mouse were determined in HEp2 cells. Naïve: Unimmunized mice, F-TM: WT F-TM VLP immunized mice, F-dcmTM: F-dcmTM VLP immunized mice, F1d-dcmTM: F1d-dcmTM VLP immunized mice, F12d-dcmTM: F12d-dcmTM VLP immunized mice, Results are presented as means±SEM and statistical analysis was performed by one-way ANOVA with Tukey's multiple comparison test in GraphPad Prism; * p<0.001,  p<0.005.
Figure 13:
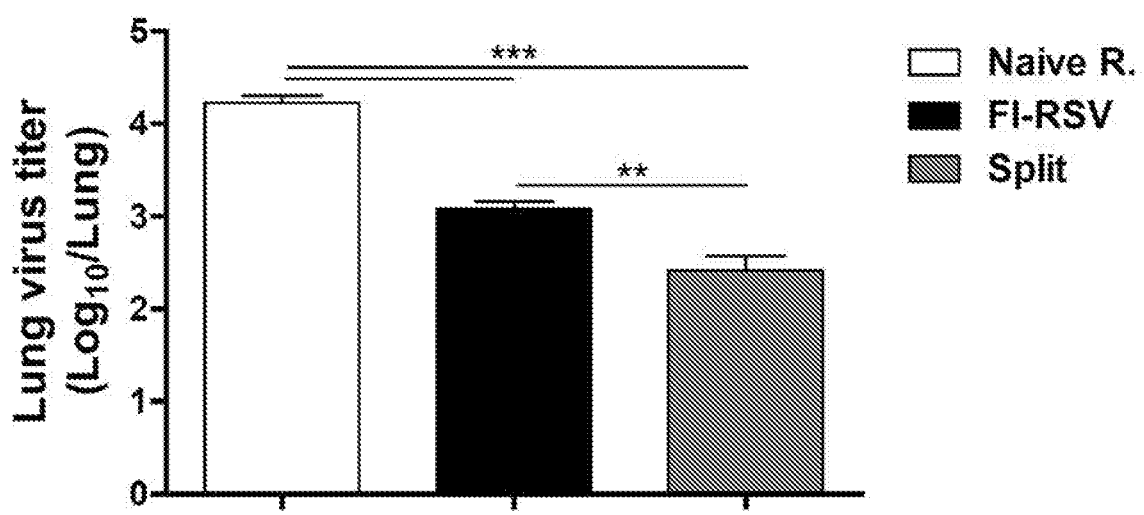
FIG. 13 shows split RSV vaccination induces more effective lung viral clearance. Adult BALB/c (5-6 weeks old) mice (N=5) were single immunized with FI-RSV (5 μg) and Split RSV (5 μg). Lung RSV titer were determined in individual lungs after RSV challenge (RSV 3.5×105 PFU/mouse) at 3 weeks after prime immunization. Naive: unimmunized mice, FI-RSV; Formalin inactivation RSV (5 μg) and Split: Formalin inactivated split RSV (5 μg). Results are representative out of two independent experiments and presented as mean±SEM. Statistical significances were performed by one-way ANOVA in GraphPad Prism; *; p<0.001, ; p<0.001 and *; p<0.05 comparing Naïve, FI-RSV and Split groups.

Neonatal age (7 days old) cotton rats (n=5) were intramuscularly immunized with split RSV (10 µg)+F DNA (25 µg), and then boosted with F VLP (10 µg) or split RSV (20 µg). Cotton rats that were prior immunized with split RSV+F DNA/F VLP or split RSV were found to clear lung viral loads after RSV challenge whereas naïve (mock control) cotton rats showed high levels of RSV titers in the lungs (FIG. 8). Most importantly, lung histopathology and inflammation were not observed in the group of cotton rats that were vaccinated with split RSV+F DNA/F VLP or split RSV after RSV challenge. These data indicates that priming split RSV+F DNA at the neonatal age of cotton rats and then boost with F VLP or split RSV can effectively induce protective immunity and prevent VED against RSV.

Example 13

Experiments were conducted to determine whether MPL+CpG adjuvanted split influenza virus vaccination improves the efficacy of cross protection against heterosubtypic influenza virus challenge. The immunized mice were challenged with rgH5N1 virus at a sublethal dose at 4 weeks post boost immunization. Body weight changes and enhanced pause of respirations (PenH) were monitored to measure severity of disease (FIG. 9A). From the day 3 post challenge, naïve infected mice and split flu vaccine only immunized mice started to lose weight (~5%), but MPL and CpG adjuvanted groups did not show body weight loss. By day 6 post challenge, the split flu vaccine only group did not show any protection (~20% weight loss) compared to the adjuvanted groups (~5-6% loss). Notably, the MPL+CpG adjuvanted group started to quickly recover body weight at day 7 post infection (FIG. 9A) and maintained the lowest PenH levels (FIG. 9B). Lung samples were collected at day 7 post infection to determine the virus titers in embryonated chicken eggs (FIG. 9B). The MPL+CpG combination group showed a significantly lower level of virus titers by 1000 folds compared to the naïve infection and split flu groups, and lower than the MPL or CpG adjuvant groups.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A respiratory syncytial virus (RSV) vaccine comprising a modified RSV F protein in a predominantly pre-fusion conformation (RSV pre-fusion F protein) presented on the surface of a virus-like particle (VLP) comprising an influenza matrix protein 1 (M1),
   wherein the RSV pre-fusion F protein comprises a transmembrane anchor domain,
   wherein the RSV pre-fusion F protein comprises one or more of the point mutations S155C, S290C, S190F, and V207L,
   wherein the RSV pre-fusion F protein comprises at least one mutation in furin cleavage site 2, wherein the at least one mutation in furin cleavage site 2 comprises an R133, R135, and/or R136 mutation,
   wherein the RSV pre-fusion F protein comprises a p27 peptide, and
   wherein the RSV pre-fusion F protein comprises a deletion of 1, 2, 3, 4, 5, 6, 7, 8, 9, or 10 of amino acid residues 138-147.

2. The vaccine of claim 1, wherein the RSV pre-fusion F protein comprises the amino acid sequence SEQ ID NO:3 or an amino acid sequence having at least 90% sequence identity to SEQ ID N0:3.

3. The vaccine of claim 1, wherein the RSV pre-fusion F protein is a fusion (F) protein further comprising a membrane anchor domain of RSV F or an influenza A hemagglutinin (HA).

4. The vaccine claim 1, wherein the VLP is produced by co-infecting insect cells with one or more recombinant baculoviruses expressing the M1 proteins and the RSV pre-fusion F protein.

5. The vaccine of claim 1, wherein the RSV pre-fusion F protein comprises a deletion of amino acid residues 138-147.

6. The vaccine of claim 1, wherein the RSV pre-fusion F protein further comprises at least one mutation in furin cleavage site 1, wherein the at least one mutation in furin cleavage site 1 comprises an R106, R108, and/or R109 mutation.

7. The vaccine of claim 6, wherein the at least one mutation in furin cleavage site 2 site 1 comprises an R106K, R108K, and R109K mutation.

8. The vaccine of claim 7, wherein the RSV pre-fusion F protein comprises S155C, S290C, S190F, and V207L mutations.

9. The vaccine of claim 6, wherein the at least one mutation in furin cleavage site 2 comprises an R133Q, R135Q, and R136Q mutation.

10. The vaccine of claim 9, wherein the RSV pre-fusion F protein comprises S155C, S290C, S190F, and V207L mutations.

11. A vaccine composition, comprising the vaccine of claim 1 in a pharmaceutically acceptable carrier.

12. A vaccine composition of claim 11, further comprising an adjuvant.

13. The vaccine composition of claim 12, wherein the adjuvant comprises low dose monophosphoryl lipid A+CpG, or cell wall skeleton of BCG.

14. A method of vaccinating a subject for respiratory syncytial virus (RSV) comprising administering the vaccine composition of claim 11 to a subject in need thereof.

* * * * *